US007697138B2

(12) United States Patent
Smith et al.

(10) Patent No.: US 7,697,138 B2
(45) Date of Patent: Apr. 13, 2010

(54) METHOD AND APPARATUS FOR DETERMINATION OF SOURCE POLARIZATION MATRIX

(75) Inventors: Adlai H. Smith, Escondido, CA (US); Robert O. Hunter, Jr., Snowmass Village, CO (US)

(73) Assignee: Litel Instruments, San Diego, CA (US)

( * ) Notice: Subject to any disclaimer, the term of this patent is extended or adjusted under 35 U.S.C. 154(b) by 469 days.

(21) Appl. No.: 11/336,532

(22) Filed: Jan. 19, 2006

(65) Prior Publication Data
US 2006/0192961 A1    Aug. 31, 2006

Related U.S. Application Data

(60) Provisional application No. 60/645,498, filed on Jan. 19, 2005.

(51) Int. Cl.
*G01J 4/00* (2006.01)
(52) U.S. Cl. ..................... 356/364; 356/369
(58) Field of Classification Search ......... 356/364–370, 356/124; 250/225
See application file for complete search history.

(56) References Cited

U.S. PATENT DOCUMENTS

| | | | |
|---|---|---|---|
| 4,158,506 A | 6/1979 | Collett | |
| 5,978,085 A | 11/1999 | Smith et al. | |
| 6,356,345 B1 | 3/2002 | McArthur et al. | |
| 6,486,940 B1 | 11/2002 | Williamson | |
| 6,741,338 B2 | 5/2004 | McArthur et al. | |
| 7,061,613 B1 * | 6/2006 | Huang et al. | 356/364 |
| 7,230,717 B2 * | 6/2007 | Brock et al. | 356/495 |
| 2003/0007151 A1 * | 1/2003 | Eckert | 356/369 |
| 2003/0234348 A1 | 12/2003 | Takeuchi et al. | |
| 2004/0114150 A1 | 6/2004 | Wegmann et al. | |
| 2004/0257564 A1 * | 12/2004 | Madsen | 356/364 |
| 2005/0099613 A1 | 5/2005 | Fukuhara | |

(Continued)

FOREIGN PATENT DOCUMENTS

EP    1 496 398 A1    1/2005

(Continued)

OTHER PUBLICATIONS

International Search Report/Written Opinion for PCT/US2006/001942 dated May 22, 2006.

(Continued)

*Primary Examiner*—Gregory J Toatley, Jr.
*Assistant Examiner*—Tri T Ton

(57) ABSTRACT

A method and apparatus for resolving both the angular (nx, ny) and spatial (x,y) dependence of the effective source coherence matrix for lithographic steppers and scanners is described. First an in-situ source metrology instrument is combined with in-situ polarization elements to create an in-situ source imaging polarizer or ISIP. The ISIP is loaded into a photolithographic exposure tool, aligned, and then exposed onto a suitable recording media or recording sensor. The recording sensor comprising either resist coated wafers or electronic sensors capture the image intensity at a multiplicity of different field points. The resulting measurements are entered into a computer program that reconstructs the source coherence matrix as a function of direction cosine at multiple field points. Alternative ISIP configurations are discussed in some detail. Applications of the ISIP include polarization source mapping for deep-UV and EUV lithography, process optimization, process monitoring, and chip manufacturing.

18 Claims, 38 Drawing Sheets

U.S. PATENT DOCUMENTS

2005/0231705 A1    10/2005    Smith et al.
2006/0192960 A1*    8/2006    Rencs et al. ............... 356/364

FOREIGN PATENT DOCUMENTS

| EP | 1 548 506 A1 | 6/2005 |
|---|---|---|
| GB | 2 352 513 A | 1/2001 |
| WO | WO 2005/106593 | 11/2005 |

OTHER PUBLICATIONS

Azzam et al., "Propagation of Polarized Light", Elsevier Science B.V., ISBN 0 444 870164, 1999 p. 148.

Baumeister, "Rudiments of the design of an immersed polarizing beam divider with a narrow spectral bandwidth and enhanced angular acceptance", Applied Optics, vol. 36, No. 16, pp. 3610-3613, Jun. 1997.

Born et al., "Principles of Optics, 7th (expanded) Edition", Cambridge University Press, pp. 268-269, 2001.

Born et al., "Principles of Optics, Coherence Matrix and Stokes Parameters", Principles of Optics, 7th (expanded) Edition, pp. 619-632, 1999.

Bruning et al., "Optical Lithography—Thirty Years and Three Orders of Magnitude", Proc. of SPIE, vol. 3051, pp. 14-27, 1997.

de Ruyter et al., "Examples of Illumination Source Effects on Imaging Performance", ARCH Chemicals Microlithography Symposium, pp. 1-8, 2003.

Harned et al., "progress report: Engineers take the EUV lithography challenge", available at the URL of oemagazine.com/fromTheMagazine/feb03euv.html, 2003.

Hecht, "Hecht, Optics Polarization and Wire Grid Polarizers", Second edition, Addison Wesley Publ, ISBN: 0-201-11609-X, p. 279, May 1990.

Hecht, "Polarization", Optics, Third Edition, Chapter 8, pp. 319-376, 1998.

Li et al., "High-performance thin-film polarizing beam splitter operating at angles greater than the critical angle", Applied Optics, vol. 39, No. 16, pp. 2754-2771, Jun. 2000.

Li, "The Design of Optical Thin Film Coatings", Optics & Photronics News, pp. 24-30, Sep. 2003.

Mandel et al., "Optical Coherence and Quantum Optics", Cambridge University Press, p. 345, 1995.

Miyake et al., "LPP-based reflectometer for EUV lithography" 1 pg.

Press et al., "Numerical Recipes, The Art of Scientific Computing", Cambridge University Press, pp. 52-64, 1990.

Schwartz, "Polarizers for extreme Ultraviolet Light", Physics 7810, 2001.

Sheppard et al., "Annular pupils, radial polarization, and superresolution", Applied Optics, vol. 43, No. 22, pp. 4322-4327, Aug. 1, 2004.

Smith et al., "Challenges in high NA, polarization, and photoresists", Proc. of SPIE, vol. 4691-2, pp. 11-24, 2002.

Thomsen et al., "Polarizing and reflective coatings based on half-wave layer pairs", Applied Optics, vol. 43, No. 22, pp. 4322-4327, Jan. 1, 1997.

">200 nm dichoric polarizer", available at the URL of www.ealingcatalog.com, pp. 84-85.

">270 nm dichoric polarizer", available at the URL of www.reynardcorp.com.

">350 nm dichoric polarizer", available at the URL of www.lasercomponents.com, 2004.

"Brewster Angle Prism", available at the URL of www.klccgo.com/glbrewster.htm.

"CVI UV Polarizing Beamsplitter Cubes", CVI Laser Optics/New Focus.

"Glan Foucault Prism", http://hyperphysics.phy-astr.gsu.edu/hbase/phyopt/polpri2.html.

"Glan Laser Prism", available at the URL of www.u-oplaz.com/table/polarizingoptics02.htm.

"Glan Taylor Prisms", available at the URL of http://www.optosigma.com/miva/merchant.mv?Screen=PROD&Store_Code=OS&Product_Code=pg175&Category_Code=Polarizers.

"Glan Thompson Polarizing Beamsplitter Cubes", available at the URL of http://www.redoptronics.com/glan-thompson-polarizing-beamsplitter-cubes.html.

"Glan Thompson Prisms", available at the URL of http://www.optosigma.com/miva/merchant.mv?Screen=PROD&Store_Code=OS&Product_Code=pg176&Category_Code=Polarizers.

"Quarter Waveplate references, devices" ThorLabs, Inc., p. 299.

"Quarter Waveplate references, theory", CVI Laser Optics and Coatings; Polarization Tutorial, pp. 204-206.

"Rochon Prism", available at the URL of www.klccgo.com/mfrochon.htm).

"Wollaston Prism", available at the URL of www.wollastonprism.com/.

* cited by examiner

Ellipsometer / Polarimeter for Preferred Embodiment (Unknown Polarization)

(L) Light Source (Unknown Polarization)
(P) Polarizing Elements
(C) SMI Camera
(O) Optics
(D) Detector or Wafer

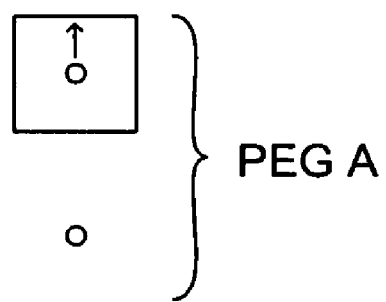
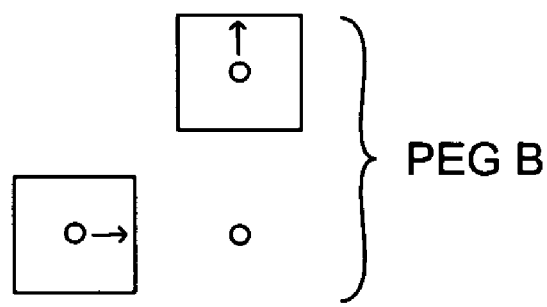
Figure 11a
Figure 11b

| x | y | nx | ny | P11 | P22 | Re(P$_{12}$) | Im(P$_{12}$) |
|---|---|---|---|---|---|---|---|
| 0 | 0 | -.4 | -.4 | 0 | 0 | 0 | 0 |
| 0 | 0 | -.2 | -.4 | 0.38 | 0.16 | 0 | 0 |
| . | . | 0 | -.4 | 0.43 | 0.20 | 0.01 | 0 |
| . | . | .2 | -.4 | . | . | . | . |
| . | . | .4 | -.4 | . | . | . | . |
| . | . | -.4 | -.2 | . | . | . | . |
| . | . | -.2 | -.2 | . | . | . | . |
| . | . | . | . | | | | |
| . | . | . | . | | | | |
| . | . | . | . | | | | |

Figure 13

METHOD AND APPARATUS FOR DETERMINATION OF SOURCE POLARIZATION MATRIX

REFERENCE TO PRIORITY DOCUMENT

This application claims priority benefit of U.S. Provisional Patent Application Ser. No. 60/645,498 filed Jan. 19, 2005 entitled "Method and Apparatus for Determination of Source Polarization Matrix" by Smith et al. Priority of the filing date of the prior application is hereby claimed, and the disclosure of the prior application is hereby incorporated by reference in its entirety.

BACKGROUND

1. Field of the Invention

The present invention relates generally to the field of semiconductor manufacturing and particularly to characterization of light sources utilized in ULSI lithography.

2. Background

Photolithography plays a vital role in semiconductor manufacturing by defining the ultimate features that are etched or deposited within each layer of the device. Projection imaging machines, usually of the stepper (see, for example, Bruning et al., "Optical Lithography—Thirty Years and Three Orders of Magitude", *Proc. of SPIE*, Vol. 3051, pp. 14-27, 1997) or step and scan (see, for example, "Optical Lithography—Thirty Years and Three Orders of Magnitude", supra) variety, typical use effective light sources that can be varied over a wide range of configurations. FIG. 1 shows a block diagram of a typical projection imaging system as would be found in a stepper or scanner. Effective source, ES, is responsible for generating and shaping the light incident on the reticle. It includes a light source, LS, (typically an excimer laser), two blocks of beam shaping optics (IIO and OIO) that produce spatially and angularly uniform light incident on reticle R. The spatial uniformity requirement is simple; it must be constant across reticle R. Angular uniformity means the angular spectrum of radiation (dE/do(nxr,nyr)) needs to be the same at all field points (e.g., x,y transverse positions on R). FIG. 2a shows in plan view the angular distribution (direction cosine coordinates nx, ny shown) of a typical source (annular quadrupole). The exact angular distribution of light within this source, the radiant intensity or dE/do(nx,ny) (energy per unit solid angle), can be measured by in-situ methods according to see, for example, U.S. Pat. No. 6,356,345, McArthur et al. "InSitu Source Metrology Instrument and Method of Use" McArthur et al., "In-Situ Source Metrology Instrument and Method of Use", U.S. Pat. No. 6,741,338, May 25, 2004, and Smith et al., "Apparatus and Method for High Resolution In-Situ Illumination Source Measurement in Projection Imaging Systems", U.S. Patent Publication No. U.S.20050231705, Oct. 20, 2005.

As photolithography pushes to k1 values below the well known Rayleigh resolution limit (k1=0.5) image enhancement techniques among which are polarized sources become crucial (see, for example, Sheppard et al., "Annular pupils, radial polarization, and superresolution", *Applied Optics*, Vol. 43, No. 22, pp. 4322-4327, Aug. 1, 2004). The effective source in FIG. 2a is polarized for enhanced resolution. Poles P2 and P4 consist of linearly polarized light in the X direction (indicated by direction of arrows in these poles) while poles P1 & P3 are Y polarized. Again, for low k1 semiconductor applications the state of polarization of the effective source is critical to lithographic performance since imaging contrast for X and Y (p and s) polarization states differ dramatically as the numerical aperture of the optical system is increased above ~0.7 (see, for example, Smith et al., "Challenges in high NA, polarization, and photoresists", *Proc. of SPIE*, Vol. 4691-2, pp. 11-24, 2002). Therefore it is desirable to have a technique that could determine the state of polarization of the effective source in a projection tool.

Exposure Sources; General Description

Quite generally, light exiting from an excimer laser or filtered mercury source, is typically described in terms of the exposure wavelength, bandwidth, and polarization. For example, 248 nm excimer laser sources have FWHM bandwidths (full wave half maximum) approaching 0.1 pm and depending on application can take on several different polarization states. Following the laser (or arc lamp) the exposure light is again modified (polarized or un-polarized) and shaped for imaging using custom illuminators. For most applications the polarization of the light impinging on the reticle is un-polarized although the industry is rapidly making use of polarized source configurations as discussed above. However, since laser beams (or filters) are never monochromatic and due to various interactions of the beam with the optical system, the polarization state of any light source is never perfect and always contains a mixture of polarized and un-polarized light; by un-polarized we mean a component that can be represented as a superposition of waves with a rapidly varying succession of different polarization states.

Polarized Light

Here, we will be mainly concerned with both polarized and un-polarized exposure sources. Polarized (or un-polarized) light can be completely characterized by four Stokes parameters S0, S1, S2, S3 (see, for example, Born et al., "Principles of Optics, Coherence Matrix and Stokes Parameters", *Principles of Optics*, $7^{th}$ (expanded) Edition, pp. 619-632, 1999) or equivalently by it's 2×2 polarization matrix (see, for example, "Principles of Optics, Coherence Matrix and Stokes Parameters", supra) (sometimes called a coherence matrix) Pij:

$$Pij = <Ei^* \mathrm{conjg}(Ej)> = |P11\, P12| \,(i,j=1:2) \quad \text{(Equation 1)}$$

$$|P21\, P22|$$

where Ei is the time varying electric field component, $<>$ denotes time averaging, and conjg( ) denotes complex conjugation. P has four components which we hereafter utilize as a four vector:

$$P=(P1,P2,P3,P4)=(P11,P22,Re(P12),Im(P12)) \quad \text{(Equation 2)}$$

Where Re/Im denote real and imaginary parts. In our apparatus, various components will be employed to further polarize or otherwise alter the state of the incident. The physical polarizing action of these components is most concisely expressed using Jones matrices (see, for example, Hecht, "Polarization", *Optics*, Third Edition, Chapter 8, pp. 319-376, 1998). To better understand this invention it is helpful to review some concepts and notation concerning the mathematical representation of polarization (see, for example, "Principles of Optics, Coherence Matrix and Stokes Parameters", supra, "Polarization", supra) and the interaction of the fields with material objects (lens, optical systems).

The transverse electric field can be defined by Equation 3:

$$E_j = e_j(\Delta v) e^{i(kz-wt+\Delta vt)} \, j=1,2 \quad \text{(Equation 3)}$$

Effect of polarizing element is to change $e_j \to e'_j$ where $$e'_k(\Delta v) = \sum_{j=1}^{2} J_{kj} e_j(\Delta v) \quad \text{(Equation 4)}$$

where $J_{kj}$ is the 2×2 Jones matrix.

The effect of successive polarizing elements is accounted for by multiplying the Jones matrices, e.g., $$e''_l(\Delta v) = \quad \text{(Equation 5)}$$
$$\sum_{j1} J2_{lj1} e'_{j1} = \sum_{j1,j2} J2_{lj1} J1_{j1j2} e_{j2} = \sum_{j2} (J2*J1)_{lj2} e_{j2}$$

Equation 5 is diagrammatically shown in FIG. 2b where light with polarization vector e is incident first on optical element 1 with Jones matrix J1 and then on optical element 2 with Jones matrix J2, the result of all this being the net system; element 1 followed by element 2, is represented by the Jones matrix J3=J2*J1 which is the matrix product of J2 and J1.

The measurable quantities are intensities and the contribution of light color $v_c + \Delta v$ ($v_c$=center or nominal frequency) is:

$$dI = \sum_k e'_k(\Delta v) e'_k{}^*(\Delta v) dv = \sum_{k,j1,j2} J_{kj1} J^*_{kj2} \quad \text{(Equation 6)}$$
$$e_{j1}(\Delta v) e^*_{j2}(\Delta v) dv$$

Integrating over frequencies, the measured intensity is:

$$I = \sum_{K,j1,j2} J_{kj1} J^*_{kj2} P_{j1j2} = \sum_{j1,j2} J*S_{j2j1} P_{j1j2} = \text{Trace}(JS*P) \quad \text{(Equation 7)}$$

where:

$$P_{j1,j2} = \langle e_{j1} e^*_{j2} \rangle \quad \text{(Equation 8)}$$
= polarization matrix of the light
= equivalent to the Stokes Parameters $$JS_{jj'} = \sum_k J^*_{kj} J_{kj'} = \sum_k J^t_{jk} J_{kj'} = (J^t J)_{jj'} = \text{Hermetian matrix} \quad \text{(Equation 9)}$$

and t denotes complex conjugate, transpose or Hermetian conjugate matrix.

The intensity (I) is expressed as:

$$I = JS_{11}*P_{11} + JS_{22}*P_{22} + JS_{12}P_{12}* + JS_{12}*P_{12} \quad \text{(Equation 10)}$$

writing I in terms of independent components of JS and P we get:

$$I = [JS_{11} \, JS_{22} \, 2*R_e(JS_{12}) \, 2*I_m(JS_{12})] \begin{bmatrix} P_{11} \\ P_{22} \\ R_e(P_{12}) \\ I_m(P_{12}) \end{bmatrix} \quad \text{(Equation 11)}$$

Now, if we do, a=1:n separate intensity measurements of the light using n different arrangements of the elements, then the net result written in matrix form is:

$$\begin{bmatrix} I^1 \\ \vdots \\ I^a \\ \vdots \\ I^n \end{bmatrix} = \quad \text{(Equation 12)}$$

$$\begin{bmatrix} JS^1_{11} & JS^1_{22} & 2*R_e(JS^1_{12}) & 2*I_m(JS^1_{12}) \\ \vdots & & & \\ JS^2_{11} & JS^2_{22} & 2*R_e(JS^2_{12}) & 2*I_m(JS^2_{12}) \\ \vdots & & & \\ JS^n_{11} & JS^n_{22} & 2*R_e(JS^n_{12}) & 2*I_m(JS^n_{12}) \end{bmatrix} \begin{bmatrix} P_{11} \\ P_{22} \\ R_e(P_{12}) \\ I_m(P_{12}) \end{bmatrix}$$

or

I = ID* P
- 4 polarization matrix components
- n x 4 design matrix
- n component measurement vector The elements of ID can be related to rows of a Mueller matrix (see, for example, Azzam et al., "Propagation of Polarized Light", *Elsevier Science B.V.*, ISBN 0 444 870164, 1999). Additional formulations can be found in see, for example, "Propagation of Polarized Light", supra: Propagation of Polarized Light, R. Azzam, chapters 2 and 3.

In-Situ Source Metrology

A technique that will be used in the practice of this invention is in-situ source metrology (see, for example, U.S. Pat. No. 6,356,345, supra and U.S. Pat. No. 6,741,338, supra and "Apparatus and Method for High Resolution In-Situ Illumination Source Measurement in Projection Imaging Systems", supra). This is required for recovering the polarization matrix, P, as a function of incident light direction (P=P(nx,ny)). Referring to FIG. 1, it generally consists of replacing reticle, R, with attached pellicle PE with either an array of pinhole cameras (see, for example, U.S. Pat. No. 6,356,345, supra and U.S. Pat. No. 6,741,338, supra) (pinhole is either above or below the reticle face) or an array of in-situ source imaging objectives (see, for example, "Apparatus and Method for High Resolution In-Situ Illumination Source Measurement in Projection Imaging Systems", supra). These three different arrangements are shown in FIG. 3 as ISMI1 (reticle backside pinhole), ISMI2 (pellicle plane pinhole), and ISMI3 (in-situ source imaging objective). Another configuration, (not shown) works in a reflective system as a transmissive pinhole array placed either prior to or after the reticle (blank, reflective reticle). In the following, the provided in-situ source metrology instrument (ISMI) will typically be combined with the polarizing elements into an integrated arrangement.

Ellipsometry

One common technique for characterizing the optical and solid-state properties of thin-films, surfaces, and material microstructure using polarized light is, ellipsometry. The basic principles (and apparatus) are described fairly easily with reference to FIG. 4a which shows a typical PCSA (Polarizer, Compensator, Sample, Analyzer) system—a more detailed discussion can be found in see, for example, "Propagation of Polarized Light", supra. First, the polarization state of an incoming inspection light (L—FIG. 4a) is typically known and possibly adjustable through the use of a polarizer (P) and compensators (C). The input light (L) is then reflected (or transmitted through) from the material (S—FIG. 4a) of interest. The interaction of the light (L) with the sample interface causes a polarization (including possible changes in phase and amplitudes) change in the input, from linear to elliptical polarization (see above discussion on polarization). The polarization change or change in the ellipse of polarization is then measured by analyzing the light reflected from the sample using a system of analyzers and detectors (A and D in FIG. 4a). In general, ellipsometry measures two values, Psi and Delta, which describe the polarization change upon interaction with the sample or optical system. For reflective systems these two values are related to the ratio of Fresnel reflection coefficients, Rp and Rs for p- and s-polarized light, respectively. Material characteristics such as film thickness, optical constants, refractive index are found by using the measured values of Psi and Delta with various material (oscillator models for example) models and algorithms to produce a system of non-trivial equations that describe the interaction of light (change in polarization) with the sample.

Polarimetry

While ellipsometry is commonly used for determining the optical properties of bulk semiconductor materials, thick layers, thin-films, and optical components as described above, it is more generally defined as a technique that can measure the state of polarization of an electromagnetic vector wave (see, for example, "Propagation of Polarized Light", supra)—also known as polarimetry. For our present discussion we will be interested in describing the novel ellipsometry/polarimetry configuration shown in FIG. 4b (compare with FIG. 4a); since, for our present work we will describe a method for determining the state of polarization of an input light source (L) using an arrangement of polarizing element groups (PEGs with known and possibly unknown properties), a reticle camera (C), and a optical system (O) with a known polarization and transmission properties (for example the Jones-pupil) for many different field points. Put another way, we seek to describe a method and apparatus for in-situ photolithographic polarimetry with the ability to determine the state of polarization of the input light source (L) as a function of direction cosine after passing through a reticle and optical system (PIO—possibly polarizing). The method of the present invention is illustrated in a flow diagram (FIG. 4c) and can easily be compared with FIGS. 4a and 4b in terms of the symbols just discussed.

It would be desirable to have a technique for determining the actual state of polarization of light incident on a reticle in a projection imaging tool that is capable of providing the polarization matrix resolved into both its transverse spatial (x,y) and angular (nx,ny) components (P=P(nx,ny;x,y)) without the use of phase shifting masks and time consuming calibrations. That is, there is a need in the art for improved methods and apparatus for determining a source polarization matrix.

SUMMARY

Techniques and apparatus for determining a polarization state of a source in a projection imaging system are described. One embodiment includes exposing at least one in-situ polarizing element group onto a recording media, followed by measuring an intensity at subcomponents within the exposed polarizing group, and reconstructing a polarization matrix of the source. Then, at least one in-situ polarization element group can be included in an in-situ source imaging polarizer. Also, the in-situ source imaging polarizer can further include a reticle. The in-situ source imaging polarizer can further include an in-situ source metrology instrument. The recording media can be on a substrate. The recording media can also be an electronic sensor.

An in-situ source metrology instrument is combined with in-situ polarization elements to create an apparatus capable of resolving both the angular (nx,ny) and spatial (x,y) dependence of the effective source coherence matrix. A recording sensor comprising either resist coated wafers or electronic sensors capture the image intensity at discrete field points. Next, these measurements are entered into a computer program that reconstructs the coherence matrix as a function of source angle and source position. The driving force for this invention stems from the continuous push towards smaller semiconductor feature size/pitch (low k1 processing). These stiff pitch and feature requirements have forced semiconductor manufacturers and lithographic tool designers (stepper and scanner manufacturers) to introduce both immersion lithography (high NA) and custom source design (dipole/quadruple polarization) for improved imaging and high circuit yields. While polarization and immersion techniques are not inherently new in the optical community their introduction and use by semiconductor manufacturers has created tough ULSI manufacturing challenges since process windows for low-k1 and high NA lithography are very small.

High NA manufacturing challenges include: 1) understanding and managing contrast loss for TM (p, X) polarized light for high NA systems (i.e. interfering electromagnetic waves have an electric field component in the z-direction and cannot be modeled with simple paraxial approximations, 2) polarization dependent aberrations (Jones-pupil), 3) mask polarization, and 4) thin-film interference (see, for example, "Challenges in high NA, polarization, and photoresists", supra). Since all of these manufacturing issues are related to the polarization of the exposure source, the ability to measure and monitor the integrity of the exposure source and illuminator becomes critical to creating processes with suitable lithographic yields. Finally, and more importantly since there are very few tools in the factory (semiconductor fab) that can rapidly and accurately measure the state of polarization of the light source on the factory floor—without disturbing day-to-day process operations or making time consuming adjustments to the optical system—the need for an in-situ polarization monitor might be even more important.

Other features and advantages of the present invention should be apparent from the following description of exemplary embodiments, which illustrate, by way of example, aspects of the invention.

BRIEF DESCRIPTION OF THE DRAWINGS

FIG. 5a shows in cross-section view an in-situ source imaging polarizer (ISIP) placed on a reticle stage (RS) in place of a reticle (R) and pellicle (PE) combination in a projection imaging tool.

FIG. 5b shows additional detail of the ISIP of FIG. 5a.

FIG. 11a shows a plan view of a single polarizing element contained in a PEG which can be used to recover some of the components of the source coherence.

FIG. 11b shows a plan view of two polarizing elements contained in a PEG which can be used to recover some of the components of the source coherence.

FIG. 13 shows the final result of the method of this invention where all polarization matrix elements are measured.

DETAILED DESCRIPTION

Figure 1:
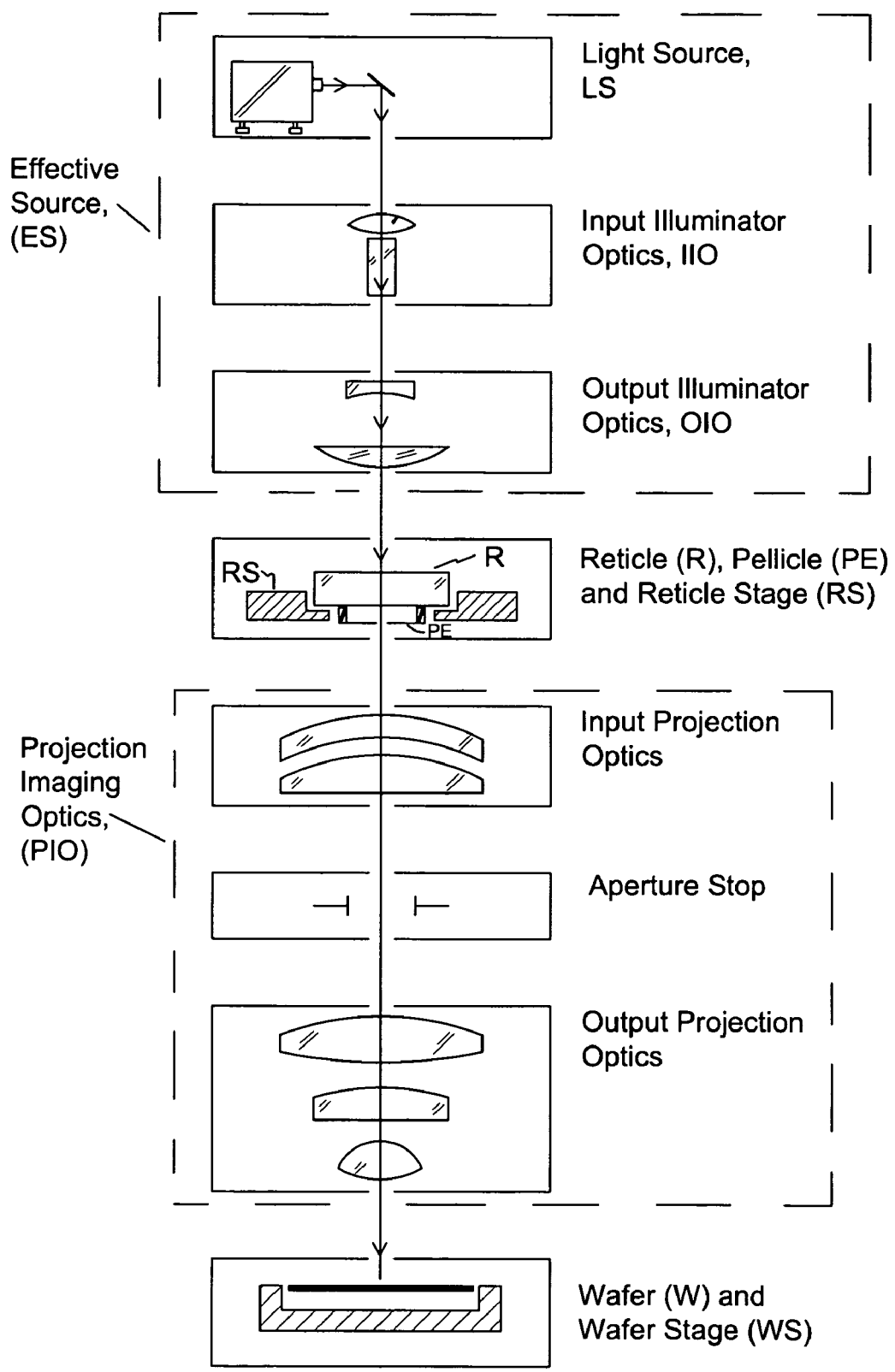
FIG. 1 is a block diagram of a projection imaging tool (stepper or scanner).

In accordance with one embodiment for determining a polarization state of a source in a projection imaging system, at least one in-situ polarizing element group is exposed onto a recording media. Measuring an intensity at subcomponents within the exposed polarizing group is then performed, followed by reconstructing a polarization matrix of the source. Then at least one in-situ polarization element group can be included in an in-situ source imaging polarizer. The in-situ source imaging polarizer can further include a reticle. The in-situ source imaging polarizer can further include an in-situ source metrology instrument.

The recording media can be on a substrate. The recording media can also be an electronic sensor.

In another embodiment, an apparatus for determining a state of polarization of a projection imaging tool includes an in-situ source metrology instrument, and an in-situ polarizing element group comprising at least one polarizing element. The in-situ source metrology instrument can include a reticle with a first surface and a second surface, and on the second surface there is a chrome coating with at least one opening in the coating. The in-situ source metrology instrument can include a reticle with a first surface and a second surface, on the first surface there is a coating with at least one opening in the coating, and an aperture plate with at least one opening, wherein the aperture plate is offset from the first reticle surface and the opening in the aperture plate corresponds to at least one opening in the coating. Additionally, the in-situ source metrology instrument can include a reticle with a first surface and a second surface, at least one lens adjacent to the second surface of the reticle, and an aperture plate mounted above the second surface of the reticle, wherein at least one opening in the aperture plate corresponds to at least one lens.

In yet another embodiment, the in-situ source metrology instrument includes a reticle with a first surface and a second surface, a first and a second reflecting prism, and a source aperture stop that is mounted horizontally on the second surface of the reticle and between the first and second reflecting prisms. In another embodiment, the in-situ source metrology instrument includes a reticle with a first surface and a second surface, at least one lens adjacent to the first surface of the reticle, and an aperture plate mounted above the second surface of the reticle, wherein at least one opening in the aperture plate corresponds to at least one lens and wherein an image of the opening in the aperture plate is at infinity. The polarizing element group may include at least two polarizing elements arranged linearly across the reticle at multiple field points. In addition, the polarizing element group may be reproduced and arranged in 2-dimensional arrays across a first surface of the in-situ source metrology instrument in such a way as to cover an entire lithographic field of interest.

Further, the polarizing element group can include four polarizing elements that are mounted to a second surface of a reticle, wherein the first polarizing element comprises a quarter-wave-plate mounted on top of and adjacent to a 45-degree sheet polarizer, the second polarizing element comprises a 45-degree sheet polarizer, the third polarizing element comprises a 90-degree sheet polarizer, and the fourth polarizing element comprises a 0-degree sheet polarizer; wherein each of the four polarizing elements is positioned and aligned to a corresponding opening in an aperture plate of the reticle. In addition, the polarizing element group may include three polarizing elements that are mounted to a second surface of a reticle, wherein the first polarizing element comprises a quarter-wave-plate mounted on top of and adjacent to a 45-degree sheet polarizer, the second polarizing element comprises a 45-degree sheet polarizer, and the third polarizing element comprises a 90-degree sheet polarizer; wherein each of the three polarizing elements is positioned and aligned to a corresponding opening in an aperture plate of the reticle. In another example, the polarizing element group may include four polarizing elements and one non-polarizing element, wherein the elements are mounted to a second surface of a reticle, wherein the first polarizing element comprises a quarter-wave-plate mounted on top of and adjacent to a 45-degree sheet polarizer, the second polarizing element represents a 45-degree sheet polarizer, the third polarizing element represents a 90-degree sheet polarizer, and the fourth polarizing element a 0-degree sheet polarizer, wherein each of the four polarizing elements is positioned and aligned to one corresponding opening in an aperture plate of the reticle and the non-polarizing element comprises an additional opening in the aperture plate of the reticle.

In another example, the polarizing element group may include two elements that are mounted to a second surface of a reticle, wherein the first element is polarizing and comprises a 90-degree sheet polarizer and is aligned to a corresponding opening in an aperture plate of a reticle and the second element is represented by an additional hole in the aperture plate of the reticle. In another example, the polarizing element group may include three elements that are mounted to a second surface of a reticle, wherein the first element is polarizing and comprises a 90-degree sheet polarizer, the second element is a 0-degree sheet polarizer, wherein both the first and second elements are positioned and aligned to a corresponding opening in an aperture plate of the reticle and the third element is represented by an additional hole in the aperture plate of the reticle. In yet another example, the polarizing element group may include three polarizing elements that are mounted to a second surface of a reticle, wherein the first element is polarizing and comprises a quarter wave plate mounted on top of and adjacent to a 45-degree sheet polarizer, the second element is a 45-degree sheet polarizer, and the third element is a 90-degree sheet polarizer, wherein each polarizing element is positioned and aligned to a corresponding opening in a aperture plate of the reticle.

The polarizing element group may also include four polarizing elements that are mounted to a first surface of a reticle, wherein the first polarizing element comprises a quarter-wave-plate mounted below a 45-degree sheet polarizer, the second polarizing element comprises a 45-degree sheet polarizer, the third polarizing element represents a 90-degree sheet polarizer, and the fourth polarizing element comprises a 0-degree sheet polarizer; wherein each of the four polarizing elements is positioned and aligned to a corresponding opening in an aperture plate of the reticle. In another example, the polarizing element group may include four polarizing elements that are mounted to a second surface of a reticle, wherein the first polarizing element comprises a quarter-wave-plate mounted below a 45-degree sheet polarizer, the second polarizing element comprises a 45-degree sheet polarizer, the third polarizing element represents a 90-degree sheet polarizer, and the fourth polarizing element comprises a 0-degree sheet polarizer; wherein each of the four polarizing elements is positioned and aligned to a corresponding chrome opening on the second surface of the reticle. In yet another example, the polarizing element group comprises four polarizing elements that are mounted to a first surface of a reticle, wherein the first polarizing element comprises a quarter-wave-plate mounted below a 45-degree sheet polarizer, the second polarizing element comprises a 45-degree sheet polarizer, the third polarizing element represents a 90-degree sheet polarizer, and the fourth polarizing element comprises a 0-degree sheet polarizer; wherein each of the four polarizing elements is positioned and aligned to a corresponding chrome opening on a second surface of the reticle described. In still another example, the polarizing element group may include four polarizing elements that are mounted to a second surface of a reticle, wherein the first polarizing element comprises a quarter-wave-plate mounted adjacent to a first 45-degree sheet polarizer, the 45-degree sheet polarizer is mounted adjacent to a first side of an aperture stop, the second polarizing element comprises a second 45-degree sheet polarizer mounted adjacent to a second side of the aperture stop, the third polarizing element comprises a 90-degree sheet polarizer mounted adjacent to the second 45 degree sheet polarizer, and the fourth polarizing element comprises a 0-degree sheet polarizer mounted adjacent to an opening in the reticle.

The polarizing element group may include four polarizing elements that are mounted to a first surface of a reticle, wherein the first polarizing element comprises a quarter-wave-plate mounted below a 45-degree sheet polarizer, the second polarizing element comprises a 45-degree sheet polarizer, the third polarizing element represents a 90-degree sheet polarizer, and the fourth polarizing element a 0-degree sheet polarizer, wherein each of the four polarizing elements is positioned and aligned to a corresponding aperture and lens. In another example, the polarizing element group may include four polarizing elements that are mounted to a second surface of a reticle adjacent an opening in an aperture plate, wherein the first polarizing element comprises a quarter-wave-plate mounted below a 45 degree sheet polarizer, the second polarizing element comprises a 45-degree sheet polarizer, the third polarizing element represents a 90-degree sheet polarizer, and the fourth polarizing element a 0-degree sheet polarizer; wherein each of the four polarizing elements is aligned to both a corresponding hole in the aperture plate and at least one lens mounted on a first surface of the reticle.

The in-situ source metrology instrument may further include a reticle with a first surface and a second surface, a chrome coating on the second surface with at least one opening in the coating, and a diffractive optical element on the first surface of the reticle configured to forming an image of the opening in the coating on the second surface of the reticle at infinity. The instrument may further include polarizing element groups including four polarizing elements that are mounted to the second surface of the reticle, wherein the first polarizing element comprises a quarter-wave-plate mounted below a 45-degree sheet polarizer, the second polarizing element comprises a 45-degree sheet polarizer, the third polarizing element represents a 90-degree sheet polarizer, and the fourth polarizing element comprises a 0-degree sheet polarizer; wherein each of the four polarizing elements is positioned and aligned to a corresponding chrome opening on the second surface of the reticle. In addition, the polarizing element group may include three polarizing elements that are mounted to the second surface of the reticle, wherein the first polarizing element comprises a quarter-wave-plate mounted below a 45-degree sheet polarizer, the second polarizing element comprises a 45-degree sheet polarizer, and the third polarizing element represents a 90-degree sheet polarizer, wherein each of the three polarizing elements is positioned and aligned to a corresponding chrome opening on the second surface of the reticle. Additionally, a state of polarization of light leaving individual polarizing elements is increased or decreased by a fixed amount.

In another embodiment, at least one element of the polarizing element group includes two 45 degree polarizing beam splitting elements mounted to a second surface of a reticle, wherein the first polarizing beam splitter divides the source into two orthogonal polarization components, one component is passed horizontally to the second beam splitter, wherein each polarizing element is aligned to a corresponding opening in an aperture plate, wherein polarized light passes through that hole. In another embodiment, at least one element of the polarizing element group includes a non-45 degree polarizing beam splitting element mounted to a second surface of a reticle, wherein the polarizing beam splitter divides the source into two orthogonal polarization components one of which is passed through a corresponding hole in an aperture plate. Additionally, at least one quarter wave plate may be included with the polarizing element that comprises two polarizing beam splitters, wherein the quarter wave plate is mounted to a reticle adjacent to and on top of the first polarizing beam splitter, under the first beam splitter on the first surface of the reticle, adjacent to and horizontal to the first beam splitter, under the second beam splitter, or under the second beam splitter on the first surface of the reticle. In another example, at least one quarter wave plate may be included with the polarizing element that comprises two polarizing beam splitters, wherein the quarter wave plate is mounted under the beam splitter on the first or second surface of the reticle.

In another embodiment, at least one element of the polarizing element group may include a polarizing beam splitter, two reflecting prisms, a Gallilean expansion telescope, and a quarter wave plate, wherein the optical elements are mounted on a second surface of a reticle, where, the first reflecting prism is mounted before the quarter wave plate, the Gallilean telescope is mounted adjacent to the quarter wave plate, the polarizing beam splitter is mounted adjacent to and after the Gallilean telescope, and the second reflecting prism is mounted after the polarizing beam splitter and is aligned to a corresponding hole in a chrome layer on a second surface of the reticle. In another embodiment, at least one element of the polarizing element group may include optical elements including a polarizing beam splitter, two reflecting prisms, two ball lenses of different diameters, and a quarter wave plate, wherein the optical elements are mounted on a second surface of a reticle, where, the first reflecting prism is mounted before the quarter wave plate, the two different diameter ball lenses are mounted adjacent to and after the quarter wave plate. The polarizing beam splitter is mounted adjacent to and after the ball lenses, and the second reflecting prism is mounted after the polarizing beam splitter and is aligned to a corresponding hole in a chrome layer on a second surface of the reticle. The polarizing elements may be Gallilean telescope or ball lenses that do not include a quarter wave plate. Additionally, a Gallilean expansion telescope may be located between the polarizing reflecting prisms on the second surface of the reticle.

In another embodiment, at least one element of polarizing element group may include two polarizing reflecting prisms mounted on a second surface of a reticle with a quarter wave plate placed between two polarizing reflective prisms. In another example, the polarizing reflecting prisms may be replaced with wire grid reflection polarizers. In addition, the polarizing element group may include at least two polarizing reflecting prisms mounted on a surface of a reticle with a quarter wave plate placed between any two of two polarizing reflective prisms. The polarizing element may be a wire grid polarizer.

In another embodiment, the polarizing element group may be operable in a reflection mode using a wire grid polarizer deposited on a silicon substrate. The wire grid polarizer may include an anti-reflective coating or no coating.

The in-situ source metrology instrument may further include at least two EUV reflecting surfaces and a plate, wherein EUV light is reflected off a first polarizing surface onto a second polarizing surface which is then reflected through a hole in an aperture plate wherein the reflections polarize the light. The reflecting surfaces may be multilayer EUV reflectors.

In another embodiment, at least one element of the polarizing element group includes optical elements including a birefringent polarizer, two reflecting prisms, and a quarter wave plate, wherein the optical elements are mounted on a second surface of a reticle, where, the first reflecting prism is mounted before the quarter wave plate, the birefringent polarizer is mounted adjacent to the quarter wave plate, and the second reflecting prism is mounted after the birefringent polarizer and is aligned to a corresponding hole in a chrome layer on the second surface of the reticle In addition, a Gallilean expansion telescope may be positioned adjacent to and following the first reflecting prism of the polarizing element group comprising birefringent polarizers. The birefringent polarizer may be a Rochon prism, a Glan Taylor Prism, a Glan Laser Prism, a Wollaston Prism, a Glan Thompson Prism, a Brewster Angle Prism, a Nicol Prism, a Glan Foucault Prism, or a Beam splitting Glan Thompson Prism.

In yet another embodiment, the in-situ polarizing element group may include a polarizer placed between an input and an output illuminator. In another example, the in-situ polarizing element group may include a light source with a known state of polarization.

Figure 4A:
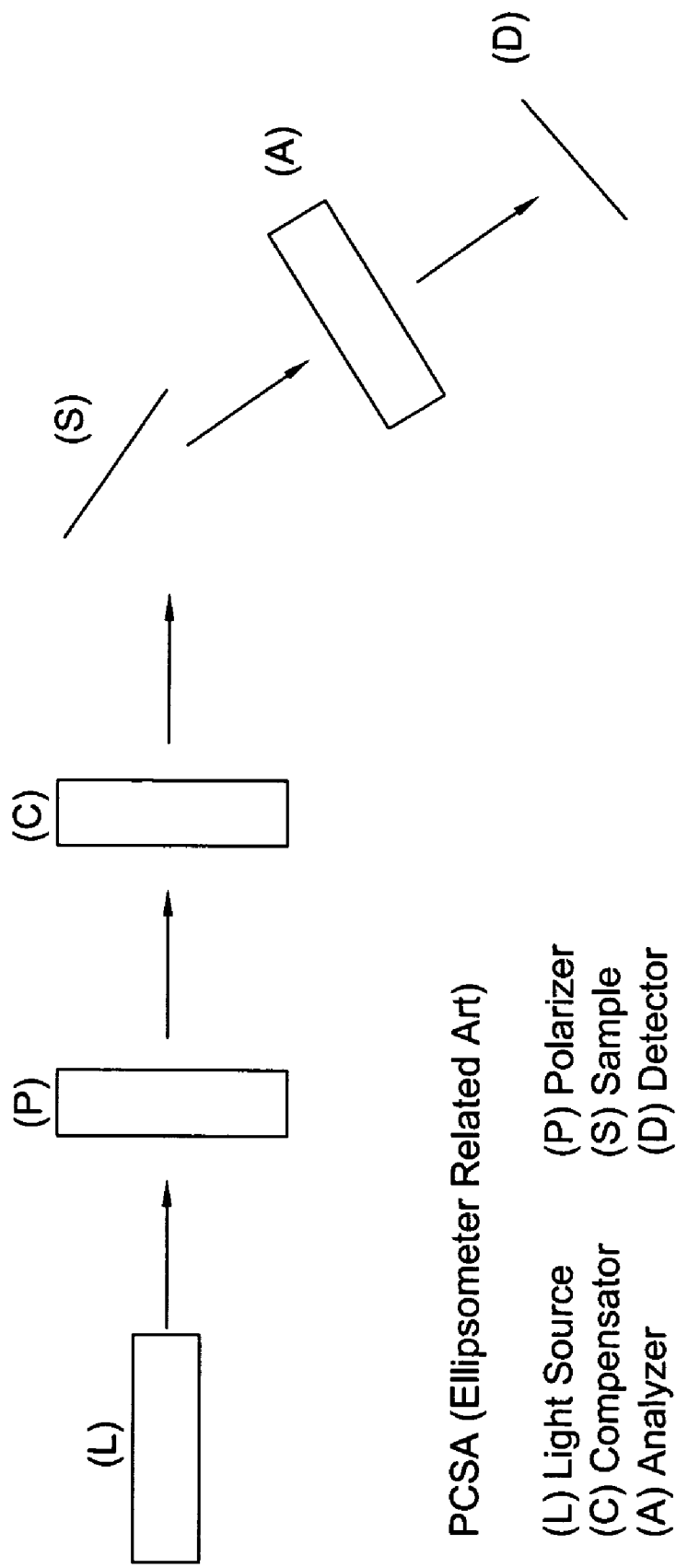
FIG. 4a shows a schematic for PCSA ellipsometry as prior art.
Figure 4B:
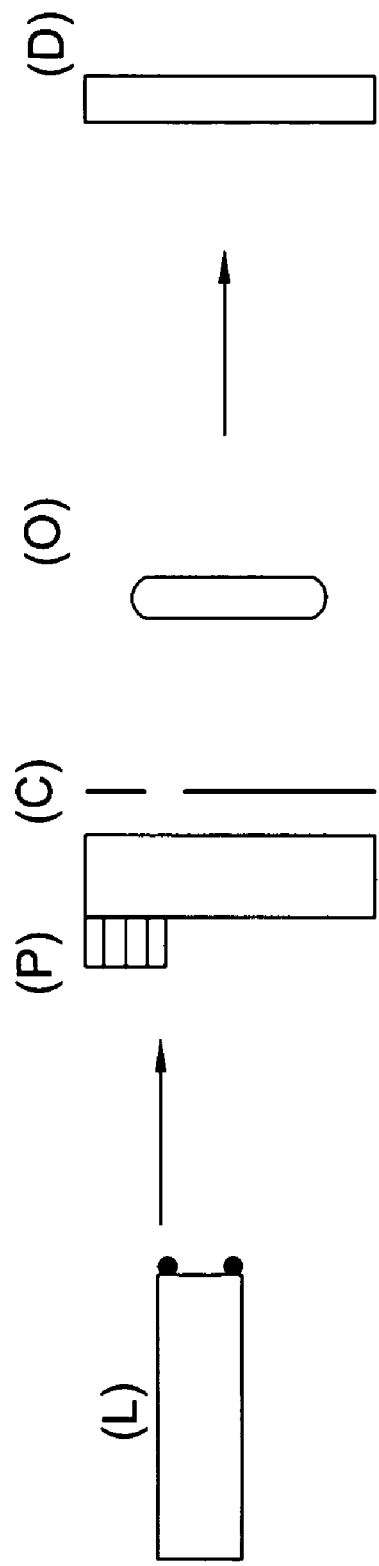
FIG. 4b shows the hardware and beam system for in-situ ellipsometry using the ISMI.
Figure 4C:
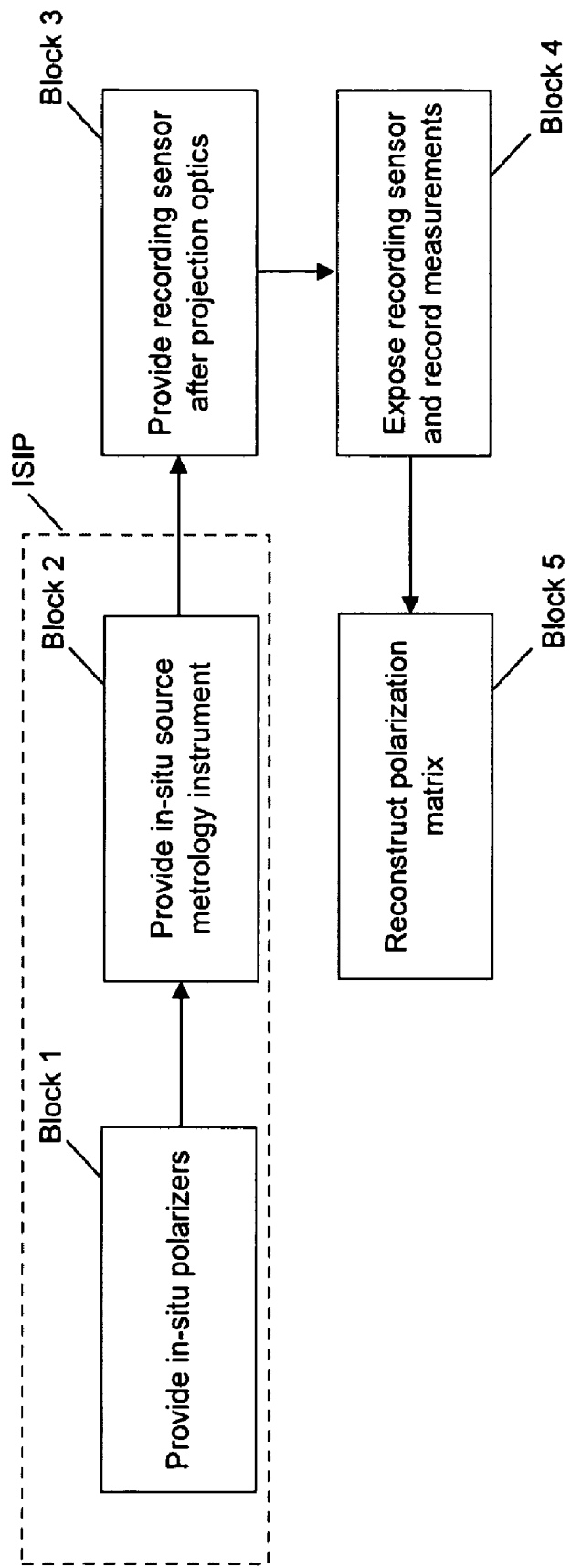
FIG. 4c is a flow chart illustrating a process for in-situ ellipsometry in a projection imaging tool.

As discussed above, the drive towards low k1 lithography warrants the use of custom polarization exposure schemes for both steppers and scanner systems used in modern ULSI applications. Additionally, since each photolithographic exposure tool company produces tools with unique illuminator designs, the polarization schemes are quite varied and require custom source inspection methodologies. FIG. 4c shows the process for in-situ ellipsometry/polarimetry of a projection imaging tool.

First Embodiment

Figures 5A, 5B:
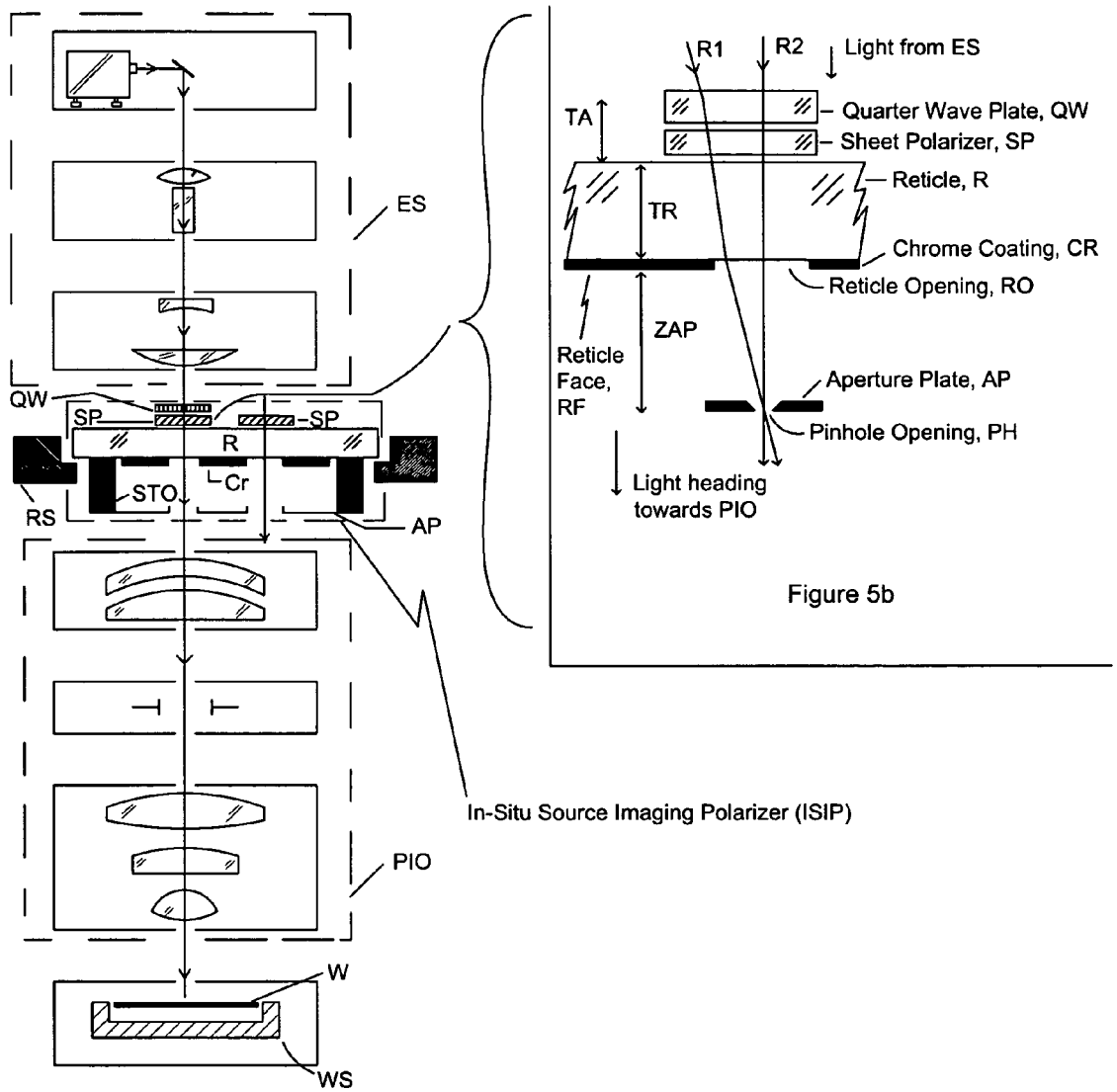

FIGS. 5a and 5b provide an overview of the apparatus and its disposition within the projection imaging tool. In FIG. 5a, in-situ source imaging polarizer (ISIP) is placed on the reticle stage and exposed as a standard reticle would be. ISIP fits within the reticle pellicle envelope of the machine so its loading also requires no special circumstances. FIG. 5*b* shows a cross section detail of a quarter wave/sheet polarizing portion of the ISIP. Rays R1 & R2 are incident from effective source ES, pass through quarter wave plate QW, sheet polarizer SP, then reticle R. Aperture plate, AP, with pinhole opening PH then encodes the ray angles as positions on the reticle (see, for example, Smith et al., "Apparatus Method of Measurement and Method of Data Analysis for Correction of Optical System", U.S. Pat. No. 5,978,085, Nov. 2, 1999 and U.S. Pat. No. 6,741,338, supra) and the light then passes through projection imaging optics PIO to wafer, W.

Provide In-Situ Polarizers: Provide In-Situ Source Metrology Instrument

Figure 6:
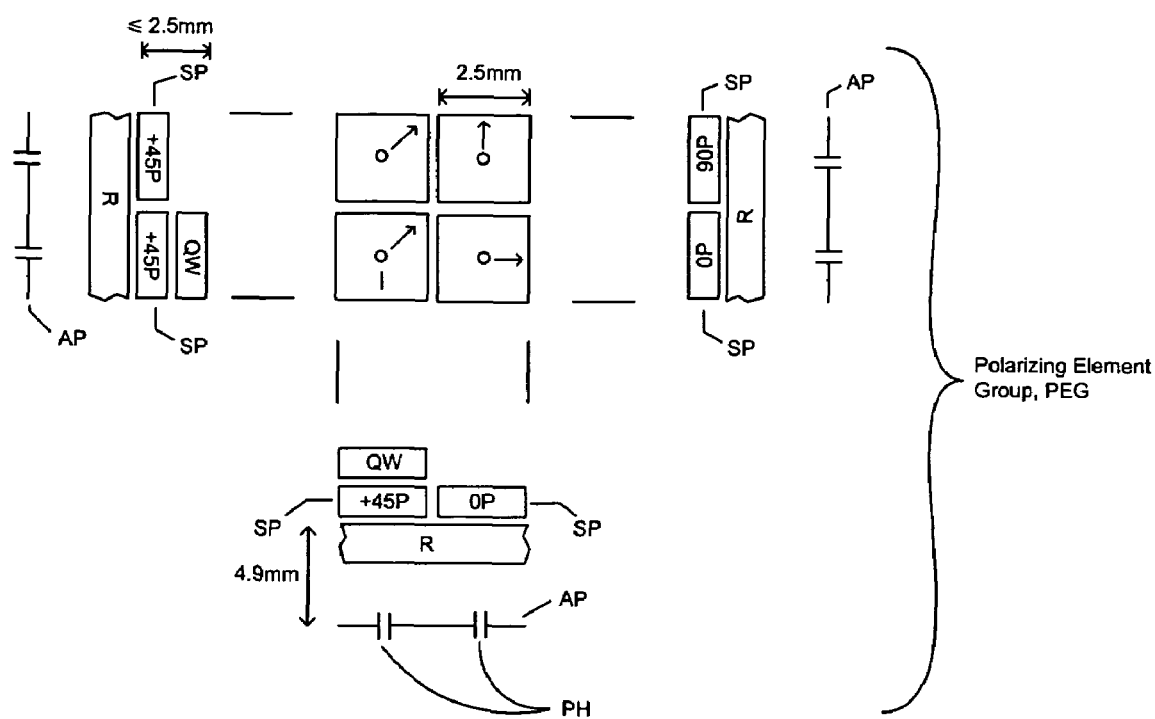
FIG. 6 is a plan view and three side views of a polarizing element group at a single field point of an ISIP.

To obtain a diverse number of polarization states typically four or more combinations of polarizing elements are combined into a single polarizing element group (PEG). The mathematical description of extracting Stokes or Jones parameters using combinations of optical elements is described nicely in the work by E. Wolf (see, for example, Mandel et al., "Optical Coherence and Quantum Optics", *Cambridge University Press*, p. 345, 1995) where typically six elements are used but four are sufficient. FIG. 6 shows a plan view and three side views of a polarizing element group at a single field point (single transverse x,y region of reticle R) of an ISIP. As shown in FIG. 6, three side views of polarizing element group at a single field point of ISIP, with NA=0.95 and M=4 geometry. In FIG. 6, single headed arrows denote polarization axis of sheet polarizers, line segments in plan view the fast axis orientation of quarter wave plates, and circle location of pinhole in aperture plate. The sizing of elements allows this device to work up to an effective source numerical aperture on the reticle side of Nas=0.95/4~0.24~14 degrees cone angle. In the plan view, the single headed arrows represent the sheet polarizer, SP, polarization direction, the straight line segment, the direction of the fast axis of the quarter wave plate, QW, while the circle is the location of pinhole PH located in aperture plate AP that is located below the reticle face. Reticle, R is approximately 3.81 mm thick while the combined sheet polarizer/quarter wave plate stack is ≦2.5 mm thick. Standoff of aperture plate, AP and pinhole PH size are as described in see, for example, McArthur et al., "In-Situ Source Metrology Instrument and Method of Use", U.S. Pat. No. 6,356,345, Mar. 12, 2002, and U.S. Pat. No. 6,741,338, supra; zap~4.9 mm while Dph~0.12 mm. Side view in FIG. 6 also spells out polarization direction of sheet polarizers, SP. Finally, we note here and in the claims below that both the order (arrangement) of PEG elements and the polarization direction of each element can be altered since for source polarization reconstruction we are more concerned with the difference in polarization between PEG elements as compared with the absolute state of polarization of each element. Many other combinations are possible as described below.

Because projection imaging tools in semiconductor lithography typically operate at single excimer wavelength or within narrow bands of Hg lamps, quarter wave plate QW can be a multiple order waveplate (e.g., it retards the relative phases of orthogonal polarizations by an integer number of wavelengths+one quarter wavelength) which is typically constructed of crystalline quartz (crystal SiO2) or possibly magnesium fluoride for use at lambda=157 & 193 nm. Other suitable uniaxial crystals can also be used (e.g., a-BBO). Crystalline waveplates operate over a wide input angle regime (>20°), can be thin (<1 mm), and of small transverse size (~2 mm). The theory of transmissive waveplates is discussed in see, for example, "Quarter Waveplate references, theory", CVI Laser Optics and Coatings; Polarization Tutorial, pp. 204-206, while examples of commercially available elements are shown in see, for example, "Quarter Waveplate references, devices", ThorLabs, Inc., p. 299.

Sheet polarizers, SP, are typically synthetic dichoric materials; they strongly absorb light polarized in one particular direction but substantially transmit the perpendicular polarization. They typically have wide input angle operating regimes (>20° cone angle). Operating principle is described in see, for example, "Quarter Waveplate references, devices", supra. For the practice of this invention, we typically require a polarization extinction ratio (transmission of maximum polarization/transmission of minimum polarization) of □ 50:1; while greater extinction ratios are certainly available and will allow for more accurate assessment of polarization state, we need to obey the packaging constraint of fitting the PEG within the reticle/pellicle envelope. See, for example, ">350 nm dichoric polarizer", available at the URL of www.lasercomponents.com, 2004, ">200 nm dichoric polarizer", available at the URL of www.ealingcatalog.com, pp. 84-85, and ">270 nm dichoric polarizer", available at the URL of www.reynardcorp.com, are examples of sheet polarizers, some of which function down to wavelength of 200 nm. Sheet polarizers such as photonic crystals or other synthetic dichoric materials or films could be useful at wavelengths below 200 nm.

Figure 3:
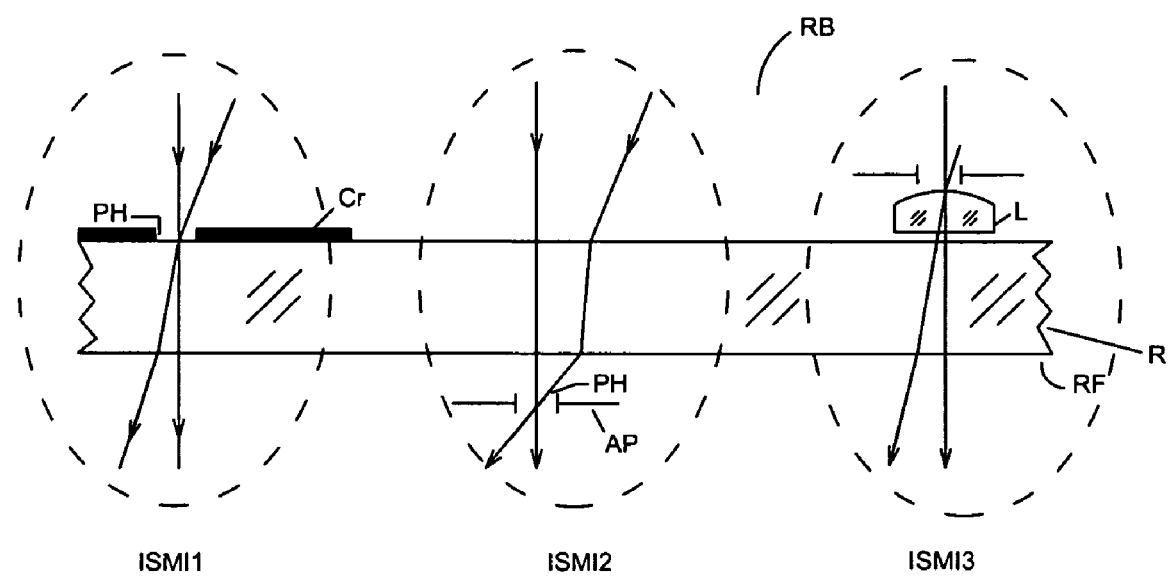
FIG. 3 shows three different in-situ source metrology instruments (ISMI) that may be utilized in practicing the invention.
Figure 7:
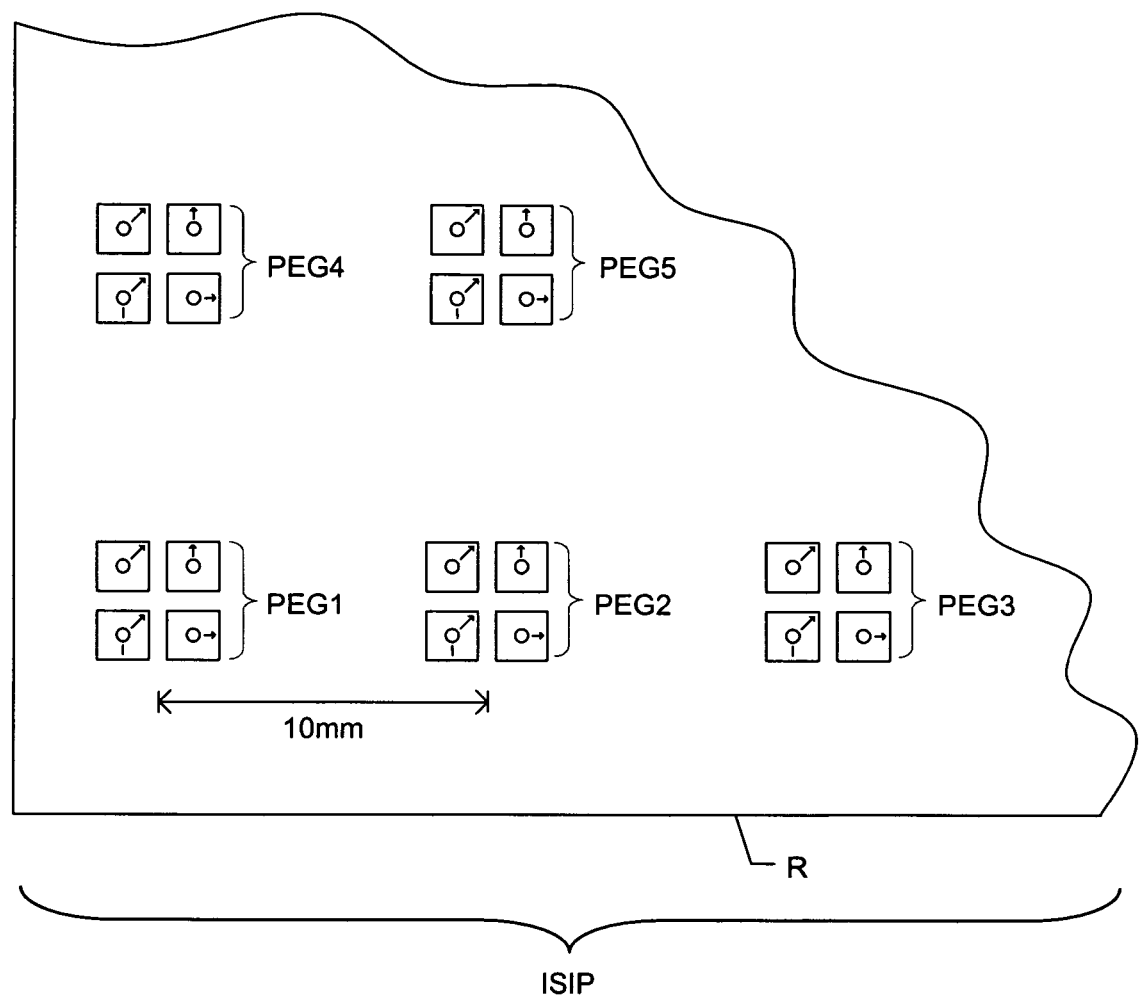
FIG. 7 shows a plan view of ISIP consisting of multiple polarizing element groups attached to reticle R.

The in-situ source metrology technique utilized in the variation of the first embodiment is the pellicle plane pinhole arrangement of see, for example, U.S. Pat. No. 6,356,345, supra and U.S. Pat. No. 6,741,338, supra and illustrated in isolation in FIG. 3, ISMI2. FIG. 7 shows a plan view of an ISIP consisting of the multiple polarizing element groups (PEG) of FIG. 6 in a rectangular array (9×11) disposed across the reticle R. Each of these PEG's correspond to 1 of 99 field points or transverse positions across the projection field at which the source coherence will be determined (x,y dependence of P).

Provide Recording Sensor After Projection Optics

Referring to FIG. 5*a*, at this point we have provided an in-situ source imaging polarizer (ISIP) and loaded it onto reticle stage RS. For the subsequent exposure step, we need to provide a recording means on the output side of projection imaging optic PIO. Typically we will utilize photoresist coated wafer, W, exposed at increasing doses as our recording means. Another alternative is an electronic sensor (typically a CCD camera with imaging optics) mounted to wafer stage, WS, that can record the intensity profile at a single PEG or PEG sub component with a single exposure, additional exposures provide the intensity profile for other PEG's or PEG sub components.

Expose Recording Sensor and Record Measurements

Figure 2A:
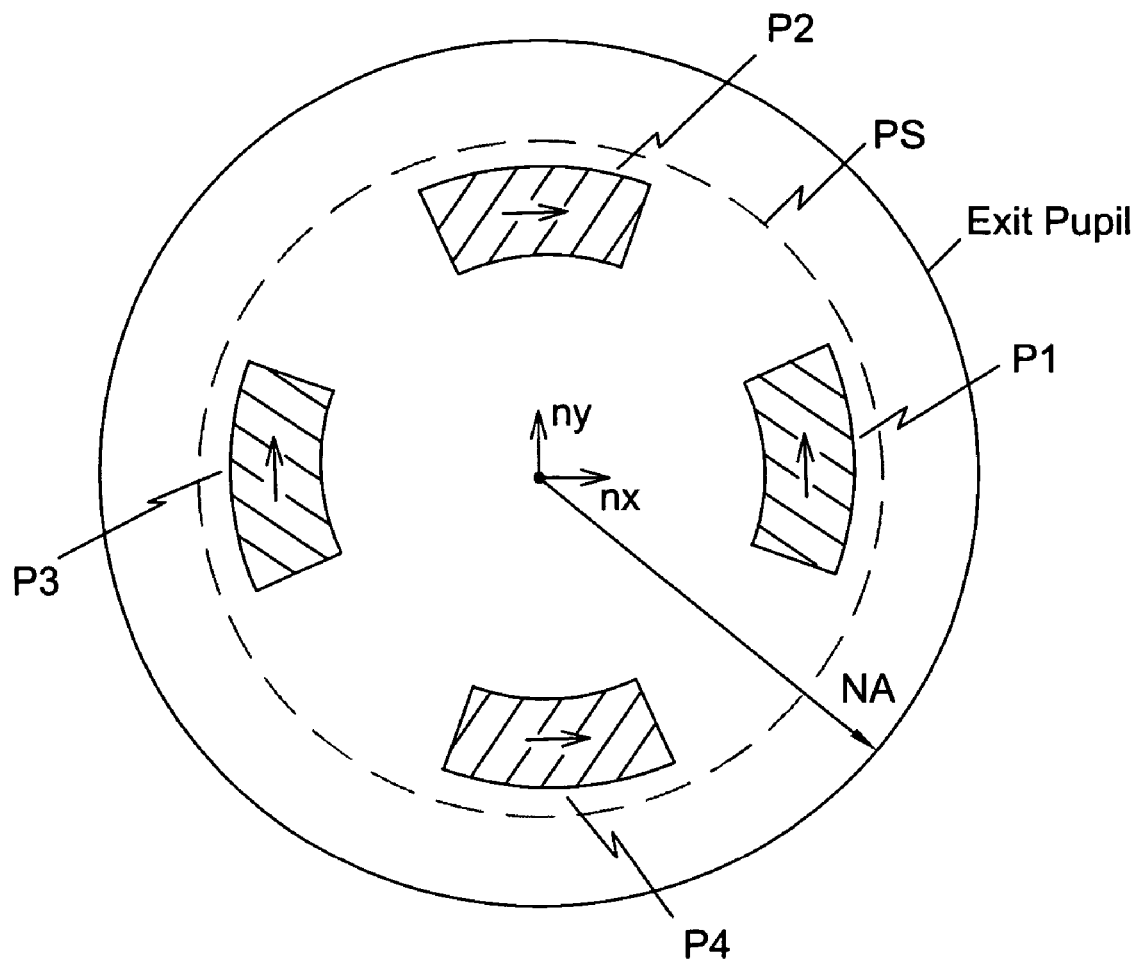
FIG. 2a is a schematic of a polarized effective source for enhanced resolution.
Figure 2B:
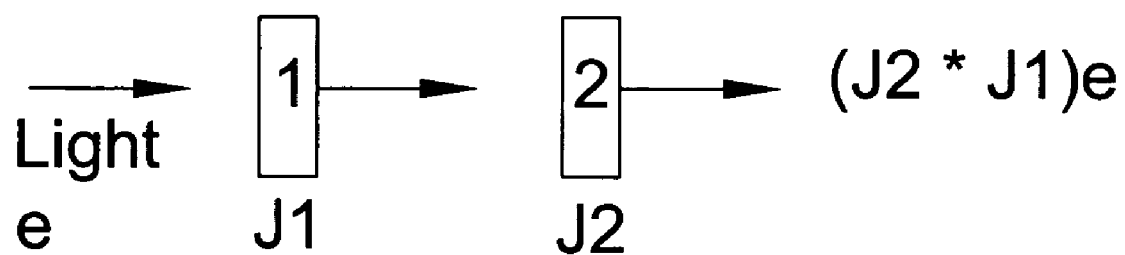
FIG. 2b shows the successive action of two polarizing elements as represented by their Jones matrices.
Figure 8:
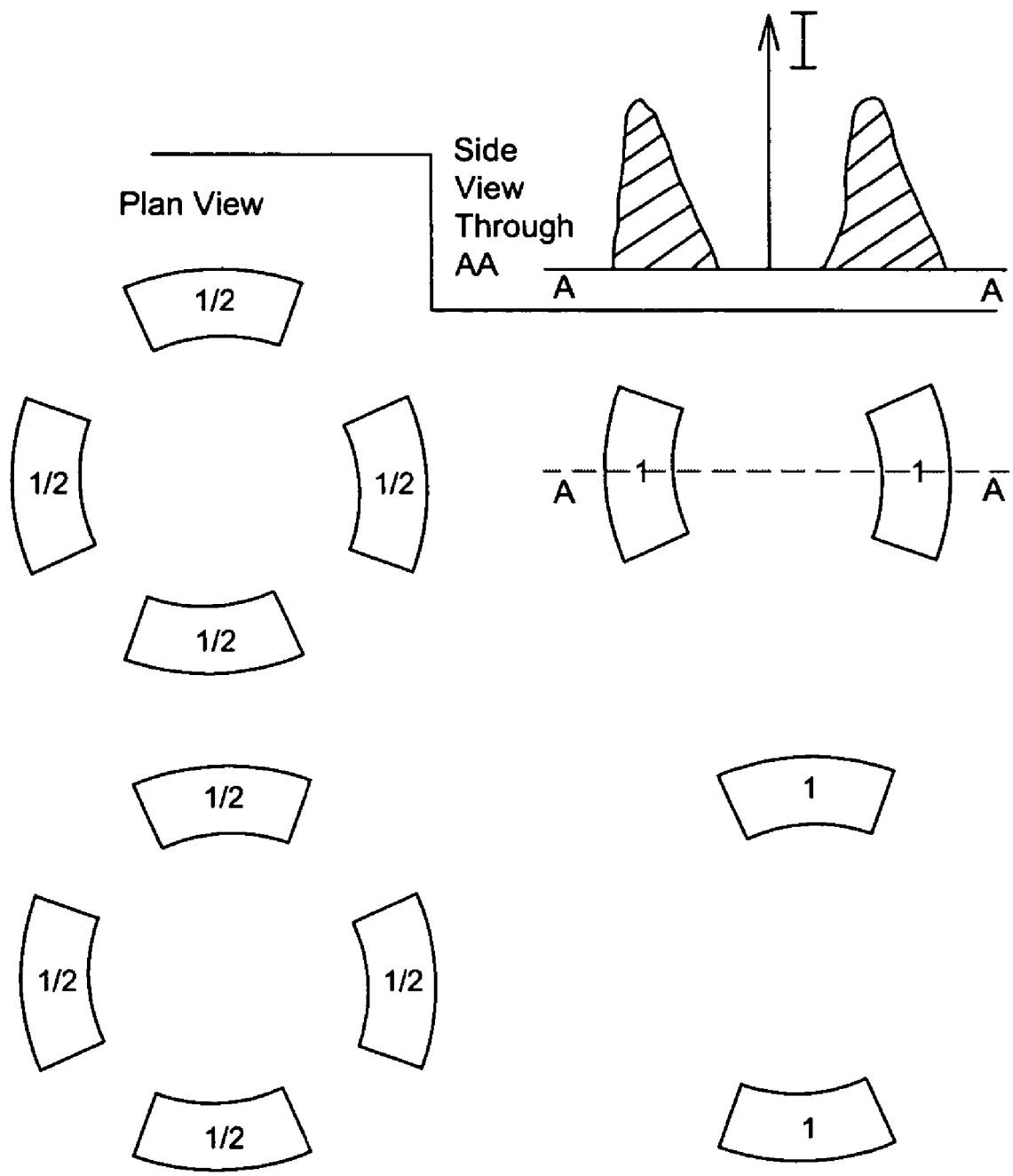
FIG. 8 shows the polarized source of FIG. 2a in the wafer plane after passing through a polarizing element group in both plan and partial cross sectional views, wherein numbers on poles indicate relative light intensity.

To better understand the structure of the images on passing through the PEG, FIG. 2*a* shows an example of a polarized effective source PS with poles P1:P4 that have differing polarization states. This PS on passing through the polarizing element group PEG1 of FIG. 7 results in an intensity pattern at the wafer plane shown (FIG. 8) in plan and partial side view through one of the poles. The numbers on each pole are the relative intensities of polarized source, PS, consisting of flat-top pole sections. Real intensity structure is indicated through cross section AA shown in side view. All four intensity patterns in the plan view need to be recorded for subsequent reconstruction.

Details of the exposure sequence will depend on the technology used for the recording means. If we use a wafer, then the exposure sequence will be as described in see, for example, de Ruyter et al., "Examples of Illumination Source Effects on Imaging Performance", *ARCH Chemicals Microlithography Symposium*, pp. 1-8, 2003, we do a dose meander with increasing exposure dose to reveal the constant intensity contours of the image passing through the PEG. An additional exposure places a reference frame around each image. The wafer is then photographed on a site by site basis and the results stored in electronic format (e.g., .bmp or .tiff). If an electronic sensor is utilized, it typically will image only a single PEG or PEG component and in this case the electronic sensor will be stepped around by wafer stage, WS, and a single exposure under the required PEG is made. Further exposures are made if information at other field points is required.

Reconstruct Polarization Matrix

The inputs for reconstruction is the intensity I(nx,ny,iPEG) at each PEG subcomponent (iPEG). This is a direct output (after scaling in x,y) from electronic recording means but involves some additional steps when a wafer is used as the recording media. These steps are described in see, for example, "Examples of Illumination Source Effects on Imaging Performance", supra and U.S. Pat. No. 6,741,338, supra and briefly amount to using the printed reference frames (vide supra) in each photo to transversely register one photo to another. The developed region within each photo corresponds to a constant intensity contour map of the desired intensity (I(nx,ny)) and by stacking them up, we get a good representation for the intensity.

Extraction of coherence matrix from measured results will depend on whether the relative net throughputs of each iPEG are known or not. The foregoing discusses both these circumstances and additionally the cases where the polarization matrix is partially reconstructed (i.e., only some components of P are determined).

Across-Field Interpolation

Since the PEGs can be arranged in arrays across the exposure field it is possible to reconstruct the Stokes parameters across a uniform grid and hence determine the state of polarization at points other than those corresponding directly to PEG elements. This can be done by using one of many methods of interpolation.

Combination 1

See the PEG of FIG. 6. There are four measurement sets linear polarizers at 0°, 45°, λ/4 plate→linear polarizer±45° and we know relative throughput of optics known in each case. For ideal components, the design matrix (ID of Equation 12) is:

$$ID = \begin{pmatrix} 1 & 0 & 0 & 0 \\ 0 & 1 & 0 & 0 \\ 1/2 & 1/2 & 1 & 0 \\ 1/2 & 1/2 & 0 & 1 \end{pmatrix} \begin{matrix} +0° \\ +90° \\ +45° \\ \pi/4 \to 45° \end{matrix} \quad \text{(Equation C1.1)}$$

The Equations to solve for polarization matrix are:

$$ID \begin{pmatrix} P_{11}(\bar{n}) \\ P_{22}(\bar{n}) \\ R_e(P_{12}(\bar{n})) \\ I_M(P_{12}(\bar{n})) \end{pmatrix} = \begin{pmatrix} \beta 1 * I_1(\bar{n}) \\ \beta 2 * I_2(\bar{n}) \\ \beta 3 * I_3(\bar{n}) \\ \beta 4 * I_4(\bar{n}) \end{pmatrix} \quad \text{(Equation C1.2)}$$

where $I_j(\bar{n})$=normalized, reconstruction for the $j^{th}$ arrangement, and $\int do_{\bar{n}} I_j(\bar{n})=1$ (normalization) (Equation C1.3). In addition, $\beta_j$=relative throughput (transmission function) for the $j^{th}$ optical arrangement; this is known by the combination of measurement and modeling. It is straightforward to solve Equation C1.2 at each $\bar{n}$ value to recover polarization matrix $P_{ij}(\bar{n})$.

Combination 2

Figure 9:
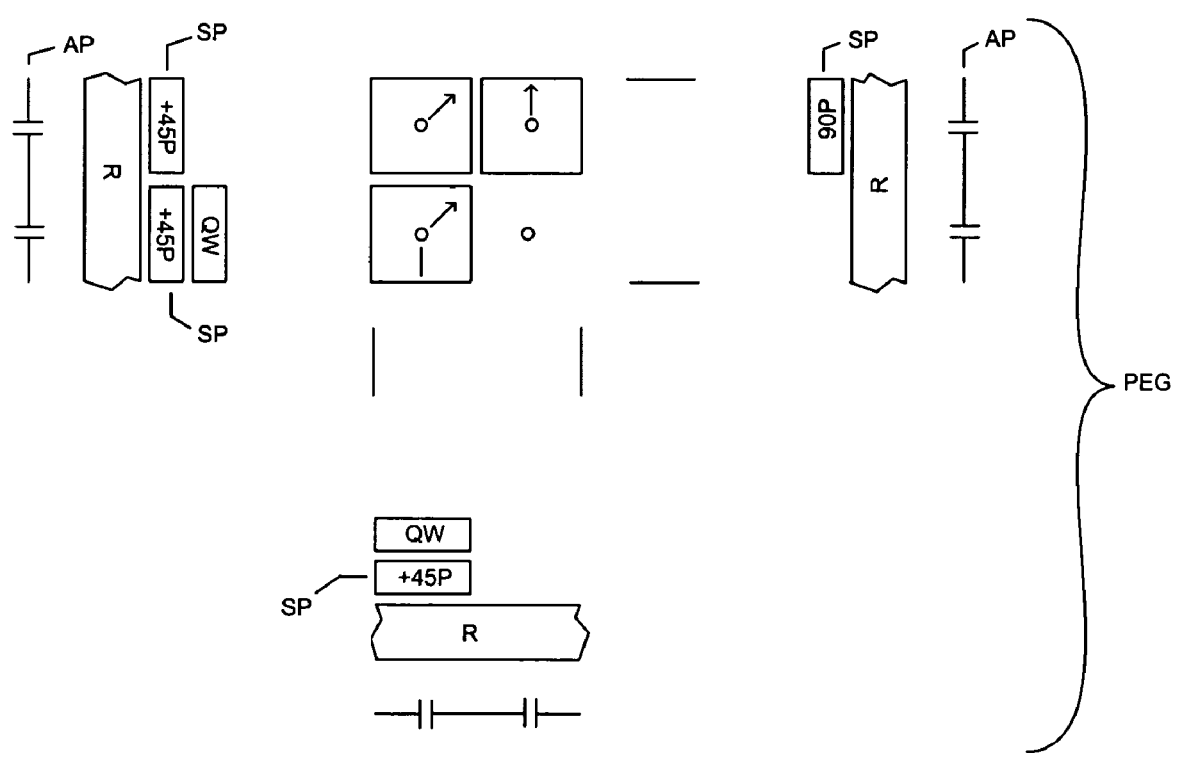
FIG. 9 shows plan view and three side views of another variation of a polarizing element group.

This arrangement (FIG. 9) is different from FIG. 6 in that the horizontal linear polarizer (+0°) is removed and we do not polarize this subcomponent. As shown in FIG. 9, the horizontal polarizer in FIG. 6 has been eliminated and no polarizing element is used and only source imaging capabilities are present.

There are four measurement sets and the relative throughput of optics is known in each case so:

$$ID = \begin{pmatrix} 1 & 1 & 0 & 0 \\ 0 & 1 & 0 & 0 \\ 1/2 & 1/2 & 1 & 0 \\ 1/2 & 1/2 & 0 & 1 \end{pmatrix} \begin{matrix} \text{no pol mod.} \\ 90° \text{ pol} \\ 45° \text{ pol} \\ \frac{\pi}{4} \to 45° \text{ pol} \end{matrix} \quad \text{(Equation C2)}$$

The equation to solve is the same as Equation C1.2. Polarization matrix, $P_{ij}(\bar{n})$, is again completely recovered.

Combination 3

This combination encompasses Combinations 1 and 2. We have m≧4 measurement sets and relative throughput of optics are known in each case.

ID=m×4 matrix corresponding to the m arrangements of polarizers and waveplates.

=rank of four matrix for complete recovery of polarization matrix.

The equation to solve is:

$$ID * \begin{pmatrix} P_{11}(\bar{n}) \\ P_{22}(\bar{n}) \\ R_e(P_{12}(\bar{n})) \\ I_M(P_{12}(\bar{n})) \end{pmatrix} = \begin{pmatrix} \beta_1 I_1(\bar{n}) \\ \beta_2 I_2(\bar{n}) \\ \vdots \\ \beta_m I_m(\bar{n}) \end{pmatrix} \quad \text{(Equation C3.1)}$$

Where $I_{j=1:m}(\bar{n})$ are the normalized (Equation C1.3), reconstructed intensities and $\beta_{j=1:m}$ are the relative throughputs of the $j^{th}$ measurement. Solve Equation C3.1 at each $\bar{n}$ by least squares methods (see, for example, Press et al., "Numerical Recipes, The Art of Scientific Computing", *Cambridge University Press*, pp. 52-64, 1990).

Combination 4

Figure 10:
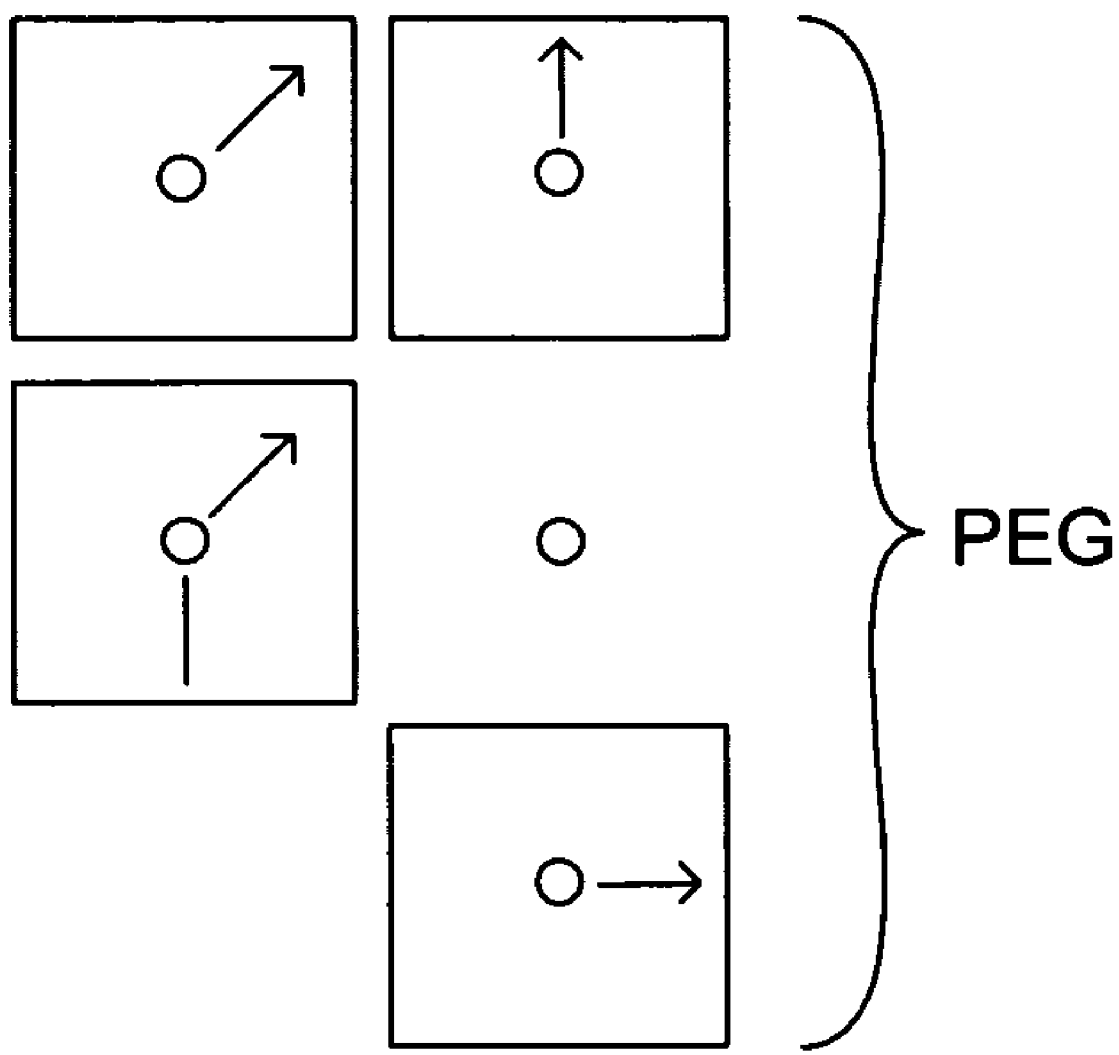
FIG. 10 shows a plan view of a polarizing element group with five components.

In this case, we have five iPEG measured intensities but the relative throughputs of each arrangement are unknown. The arrangement of elements in this case is as in FIG. 10; it is the same arrangement as in FIG. 6 only there is an additional unpolarized element. Using the PEG illustrated in FIG. 10, data gathered can be used to reconstruct a source coherence, even if the relative net throughputs of each component is unknown a priori.

There are a total of five measurement sets or arrangements.

The design matrix ID is:

$$ID = \begin{pmatrix} 1 & 1 & 0 & 0 \\ 0 & 1 & 0 & 0 \\ 1 & 0 & 0 & 0 \\ 1/2 & 1/2 & -1 & 0 \\ 1/2 & 1/2 & 0 & 1 \end{pmatrix} \begin{matrix} \text{none} \\ +90° \\ 0° \\ -45° \\ \frac{\lambda}{4} \to 45° \end{matrix} \quad \text{(Equation C4.1)}$$

The equation to solve for the polarization matrix is:

$$ID * \begin{pmatrix} P_{11}(\bar{n}) \\ P_{22}(\bar{n}) \\ R_e P_{12}(\bar{n}) \\ I_M P_{12}(\bar{n}) \end{pmatrix} = \begin{pmatrix} \beta_1 I_1(\bar{n}) \\ \vdots \\ \beta_5 I_5(\bar{n}) \end{pmatrix} \quad \text{(Equation C4.2)}$$

$I_j(\bar{n})$ normalized per Equation C1.3 and $\beta_1 \ldots \beta_5$ are five unknown constants. ID is a 5×4 matrix with one linear relation between its rows, namely:

$$\beta_2 I_2(\bar{n})+\beta_3 I_3(\bar{n})+\beta_4 I_4(\bar{n})+\beta_5 I_5(\bar{n})=2\beta_1 I_1(\bar{n}) \quad \text{(Equation C4.3)}$$

We can set $\beta_1=1$ since it provides an overall scale (or normalization) and then solve for $\beta_2, \ldots \beta_5$ by moments or correlation matrix method.

Moments Method

With $\beta_1=1$, multiply Equation C4.3 by $Z_l(\bar{n}/NA_s)$ and integrate over $d^2n$. Here $Z_l(\bar{x})$ is the lth Zernike polynomial and $NA_s$ is some estimate of the source NA under consideration. j runs over the values 2:5 and l=1:K≧4 resulting in the equations:

$$\sum_{j=2}^{5} M_{lj} \beta_j = 2M_{1j} \quad \text{(Equation C4.4)}$$

where:

$$M_{lj} = \int d^2 n Z_l\left(\frac{\bar{n}}{NA_s}\right) I_j(\bar{n}) \quad \text{(Equation C4.5)}$$

Equation C4.4 can then be solved for $\beta_2 \ldots \beta_5$.

Correlation Matrix Method

With $\beta_1=1$, multiply Equation C4.3 by $I_l(\bar{n})$ (l=1:5) and integrate $\int do_{\bar{n}}$ to get the equations:

$$\sum_{j=2}^{5} E_{lj} \beta_j = 2E_{l1} \quad \text{(Equation C4.6)}$$

where $$E_{lj} = \int do_{\bar{n}} I_l(\bar{n}) I_j(\bar{n}) \quad \text{(Equation C4.7)}$$

Equation C4.6 can then be solved for $\beta_2 \ldots \beta_5$.

Combination 5

This is the general case where the relative throughputs within the arrangements (iPEGS) are unknown.

The conditions are:
m≧5 measurement sets or arrangements
relative throughput of optics unknown
ID=m×5 matrix of arrangements
=rank 4 matrix It must have the additional property that at least one linear combination in the subspace perpendicular to the singular values contains all β values. Put differently, if we do a singular value decomposition of ID:

$$ID=U\Sigma V^T \quad \text{(Equation C5.1)}$$

where
U=m×m orthogonal matrix
Σ=m×4 singular value matrix
V=4×4 orthogonal matrix then in the course of solving the equations $$ID * \begin{pmatrix} P_{11}(\bar{n}) \\ P_{22}(\bar{n}) \\ R_e(P_{12}(\bar{n})) \\ I_m(P_{12}(\bar{n})) \end{pmatrix} = \begin{pmatrix} \beta_1 I_1(\bar{n}) \\ \beta_2 I_2(\bar{n}) \\ \vdots \\ \beta_m I_m(\bar{n}) \end{pmatrix} \quad \text{(Equation C5.2)}$$

Using the decomposition of Equation C5.1, the following (m−4) conditions $$\sum_{K=1}^{m} U_{jk} \beta_j I_j(\bar{n}) = 0 \quad K = 5:M \quad \text{(Equation C5.3)}$$

must be obtained.

Multiply Equation C5.3 by $I_{l=1:m}(\bar{n})$ and integrating $\int do_{\bar{n}}$ we set the m*(m−4) equations:

$$\sum_{j=1}^{m} U_{jk} \beta_j E_{jl} = 0 \quad \text{(Equation C5.4)}$$

where $$E_{jl} = \int do_{\bar{n}} I_l(\bar{n}) I_j(\bar{n}) \quad \text{(Equation C5.5)}$$

So the matrix multiplying the vector $\beta_j$ must have rank:m. The solution for the $\beta_j$ is then the zero singular values of this matrix.

Combination 6

FIG. 11b, PEGB, three sets. V, H, none. Unknown relative throughput $$ID = \begin{pmatrix} 1 & 1 & 0 & 0 \\ 1 & 0 & 0 & 0 \\ 0 & 1 & 0 & 0 \end{pmatrix} \begin{matrix} \text{no pol} \\ V \text{ pol} \\ H \text{ pol} \end{matrix}$$

Equation to solve analogous to Equation C4.2. Apply method in Combination 5 to get $\beta_1$, $\beta_2$, $\beta_3$. Then solve for $P_{11}(\overline{n})$, $P_{22}(\overline{n})$.

Combination 7

Partial extraction of coherence matrix parameters when relative throughputs are known. PEGA of FIG. 11a contains two measurement sets; no polarization and vertical polarization.

$$ID = \begin{pmatrix} 1 & 1 & 0 & 0 \\ 0 & 1 & 0 & 0 \end{pmatrix} \begin{matrix} \text{none} \\ \text{vertical } pol \end{matrix}$$

Equation to solve for polarization matrix is:

$$ID \begin{pmatrix} P_{11}(\overline{n}) \\ P_{22}(\overline{n}) \\ R_e(P_{12}^{(n)}) \\ I_M(P_{12}\overline{n}) \end{pmatrix} = \begin{pmatrix} \beta_1 I_1(\overline{n}) \\ \beta_2 I_2(\overline{n}) \end{pmatrix} \quad \text{(Equation C6.1)}$$

$\beta_j$, $I_j(\overline{n})$ known. Solve via, for example, "Numerical Recipes, The Art of Scientific Computing", supra, to get $P_{11}$ and $P_{22}$.

So at this point we have extracted some or all of the components of the polarization matrix P(nx,ny) (spatial indices x,y dropped) that represents the effective source, ES. There is a general influence of projection imaging optic (PIO, FIG. 5a) on our results that is correctible.

Figure 12:
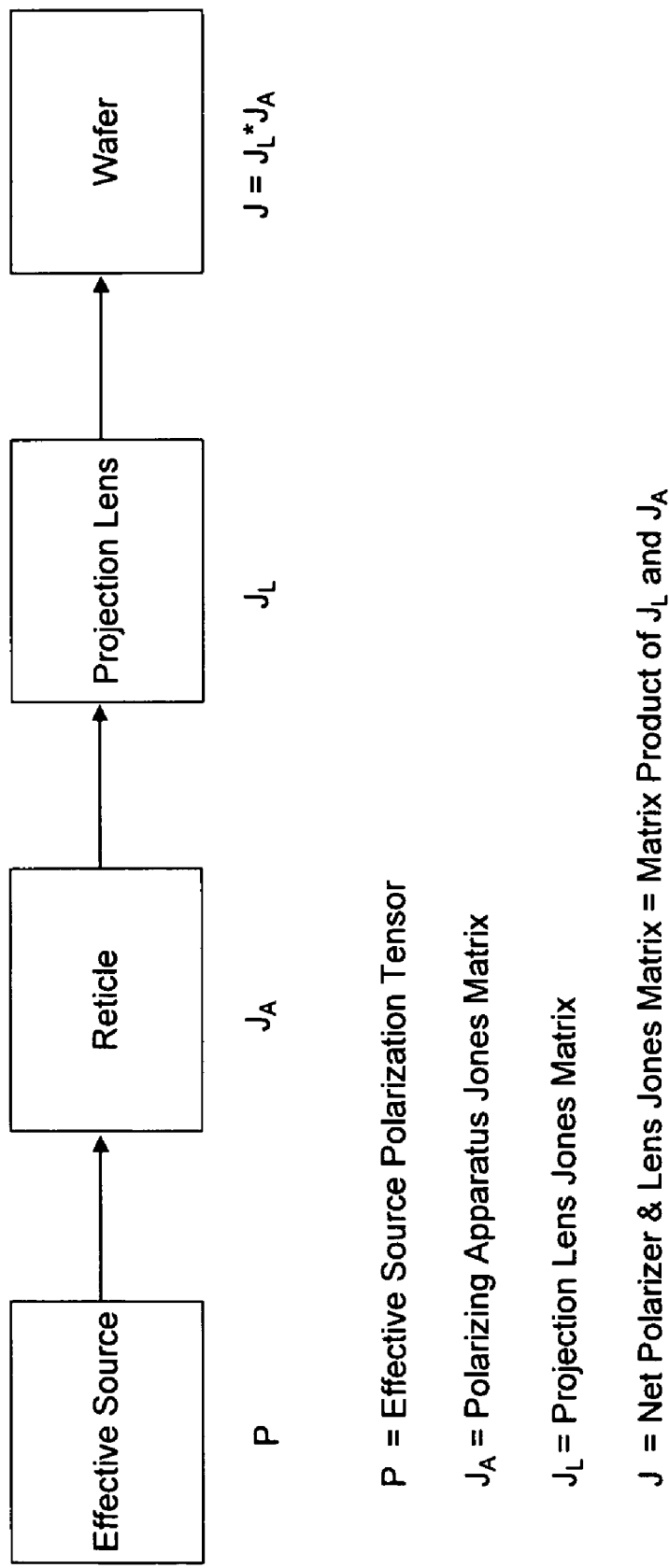
FIG. 12 shows a combination of projection imaging optics and in-situ reticle polarizers expressed as a Jones matrix.

A lens will generally attenuate, aberrate and polarize the incident light. Since the lens or projection optic follows the polarizing arrangement, the lens Jones matrix will multiply it. Sequence of light propagation by subsystem is shown in FIG. 12.

The propagator for polarization states is $$J^t J = J_A^t J_L^t J_L J_A \quad \text{(Equation LM1)}$$

(t is Hermitian conjugate)

and the intensity at the wafer is:

$$I = T_r(J^t J P) = T_r(J_A^t J_L^t J_L J_A P) \quad \text{(Equation LM2)}$$

$J_L$ will generally be a function of $\overline{n}(J_L(\overline{n}))$. For a non-birefringent, non-dichoric (e.g., optically isotropic) lens we have, $$J_L(\overline{n}) = \sqrt{T(\overline{n})} \, e^{i\phi(\overline{n})} \begin{bmatrix} 1 & 0 \\ 0 & 1 \end{bmatrix} \quad \text{(Equation LM3)}$$

where;

$T(\overline{n})$ = lens transmission $\phi(\overline{n})$ = lens phase aberration The effect on polarization transfer is completely set by $J^t J$ so that for an isotropic lens, Equation LM2 reduces to scalar multiplication by the transmission:

$$I(\overline{n}) = T(\overline{n}) T_r(J_A^t J_A P) \quad \text{(Equation LM4)}$$

The above equation does not take into account the finite angular ($\overline{n}$) resolution of our analyzing device, but this can be resolved (vide infra).

Therefore, and in this case, we can interpret all our previous results as having reconstructed the product: $T(\overline{n})P(\overline{n})$. So if we otherwise know $T(\overline{n})$ we can divide out its effect on the final result.

When the lens is not isotropic we generally require more information concerning $J_L^t J_L$ to make this method work. For example, the lens design of see, for example, Williamson, "High Numerical Aperture Catadioptric Lens", U.S. Pat. No. 6,486,940, Nov. 26, 2002 contains multiple wave plates disposed before and after a beam splitting cube. Ideally, this system would have the Jones matrix:

$$J_L(\overline{n}) = \sqrt{T(\overline{n})} \cdot e^{i\phi(\overline{n})} \begin{bmatrix} -\frac{1}{\sqrt{2}} & 0 \\ -\frac{i}{\sqrt{2}} & 0 \end{bmatrix} \quad \text{(Equation LM5)}$$

and $$J_L^t J_L(\overline{n}) = T(\overline{n}) \begin{bmatrix} 1 & 0 \\ 0 & 0 \end{bmatrix} \quad \text{(Equation LM6)}$$

Repeating the analysis sequence of Combination 1, calculation of the ID matrix using the lens transfer matrix of Equation LM6 gives:

$$ID = T(\overline{n}) \begin{bmatrix} \frac{1}{4} & \frac{1}{4} & \frac{1}{2} & 0 \\ \frac{1}{4} & \frac{1}{4} & -\frac{1}{2} & 0 \\ \frac{1}{4} & \frac{1}{4} & 0 & \frac{1}{2} \\ \frac{1}{4} & \frac{1}{4} & 0 & -\frac{1}{2} \end{bmatrix} \begin{matrix} +45° \\ -45° \\ \frac{\lambda}{4} \rightarrow 45° \\ \frac{\lambda}{4} \rightarrow -45° \end{matrix}$$

So, except for the $T(\overline{n})$ factor, we can proceed as in Combination 1 to recover the polarization matrix.

Finite Angular Resolution

Effect of finite angular resolution is expressed as:

$$B_j I_j(\overline{n}) = ID_j \int do_{\overline{m}} P(\overline{n}+\overline{m}) T(\alpha\overline{n}+\overline{m}) B(\overline{m}) \quad \text{(Equation FA1)}$$

where;

$ID_j = j^{th}$ row of design matrix and $\alpha$, B depend on in-situ imaging technology according to (see FIG. 3):

Pinhole camera: (above or below reticle face) $\alpha = 1$ $B(\overline{m}) = \Theta(|\overline{m}| \leq NA_{pH})$ In-situ imaging objective: $\alpha = 1$ $B(\overline{m}) = \Theta(|\overline{m}| \leq NA_I)$ Infinity imaging objective: $\alpha = 0$ $B(\overline{m}) = \Theta(|\overline{m}| \leq NA_{Ph})$ The use of all this is that if we know the lens transmission $T(\overline{n})$ then after solving for the polarization components we have:

$Kn_K(\overline{n})$=Known or solved for polarization component=$\int do_{\overline{m}} P_K(\overline{n}+\overline{m}) T(\alpha\overline{n}+\overline{m}) B(\overline{m})$ (Equation FA2)

and we can either deconvolve for $P_K$ or at least make the correction:

$$P_K^{used}(\overline{n}) = \frac{Kn_K(\overline{n})}{T(\alpha\overline{n})} \approx \int do_{\overline{m}} P_K(\overline{n}+\overline{m}) B(\overline{m}) \quad \text{(Equation FA3)}$$

So, at worst, our resolution is blurred by convolution.

The final result of the method of this invention is shown in FIG. 13. There the unique components of the polarization or coherence matrix are listed as a function of transverse position x,y and incident direction cosine nx,ny.

Further Arrangements

Figure 14:
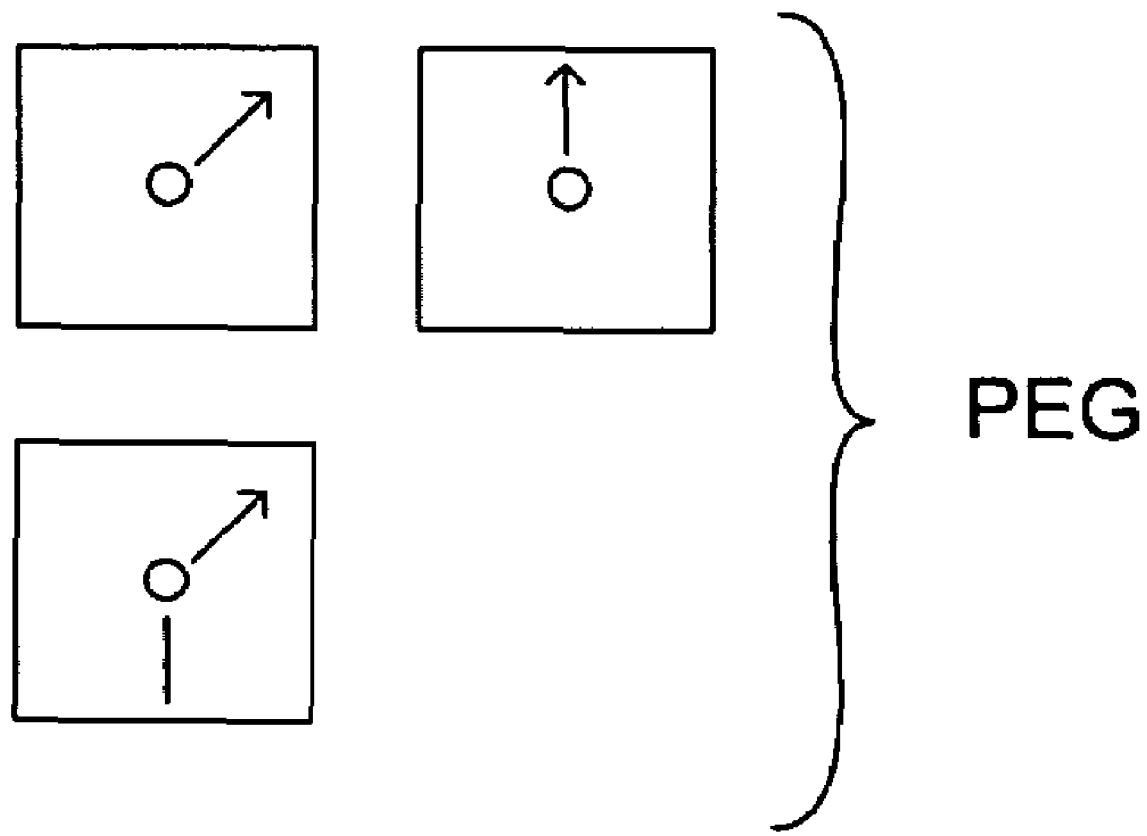
FIG. 14 shows a plan view of a polarizing element group containing only three components.

FIG. 14 shows a plan view of a PEG containing only three components. Data gathered from this PEG can be combined with unpolarized source metrology instruments (see, for example, U.S. Pat. No. 6,356,345, supra and U.S. Pat. No. 6,741,338, supra and U.S. Patent Publication No. 20050231705, supra) to reconstruct the complete source coherence since we get intensity information for the entire source as a function of solid angle.

Figure 15:
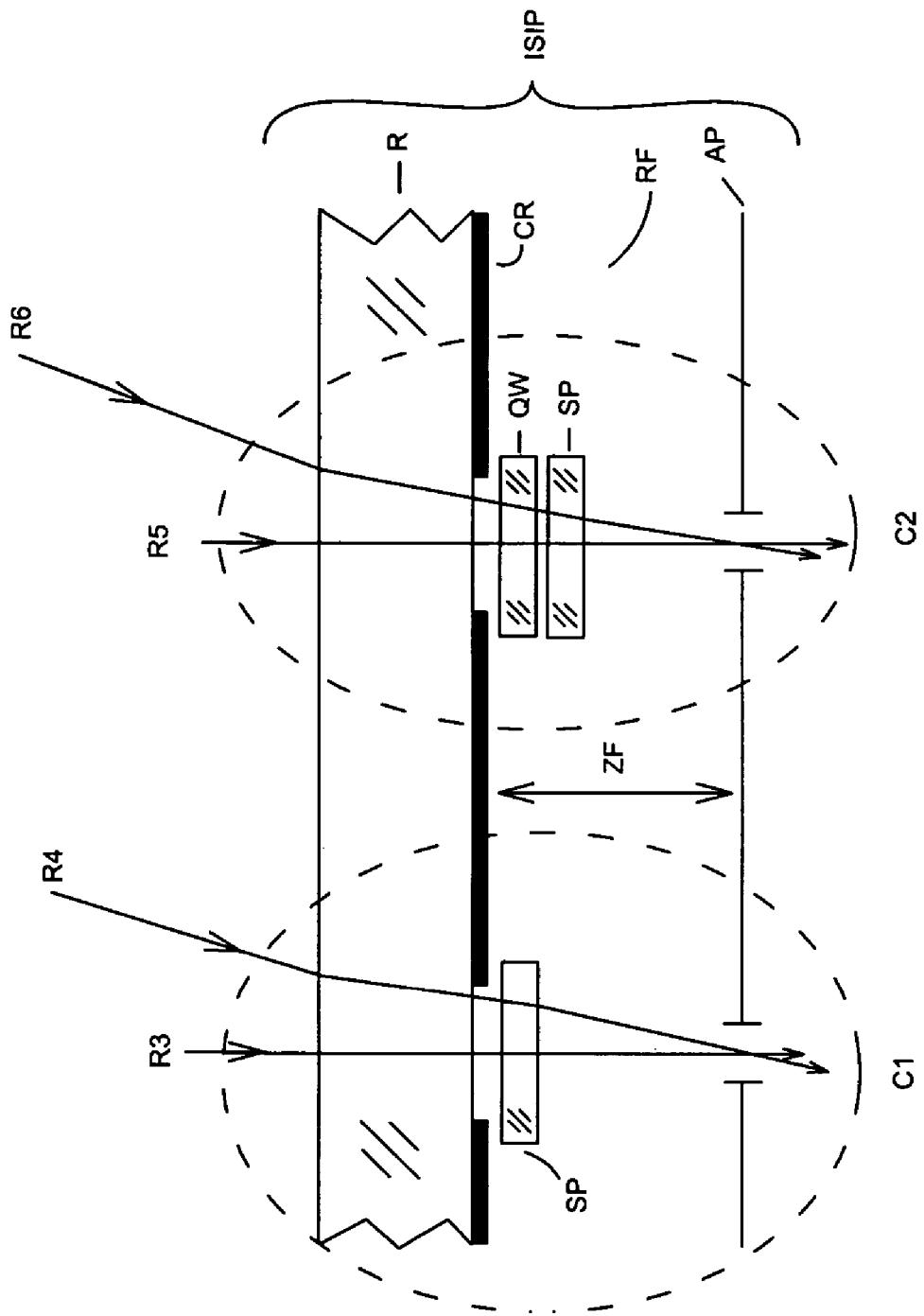
FIG. 15 shows two components (C1 & C2) in a polarizing element group of another arrangement of the first embodiment.

FIG. 15 shows two components (iPEGs) (C1 and C2) of a multicomponent PEG in another arrangement of the first embodiment. Sheet polarizers, SP, and quarter wave plates, QW, are located on reticle face, RF. In this arrangement, more space is available for polarizing elements and there is also no distortion due to the thickness variation of either SP or QW.

Figure 16:
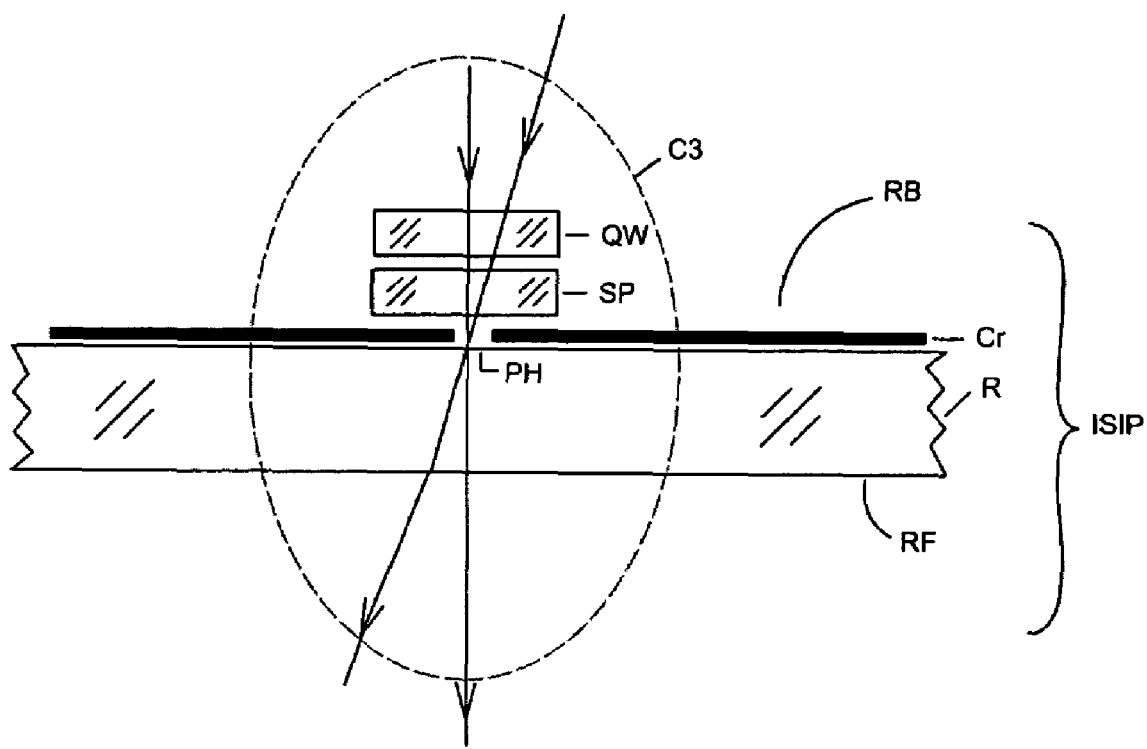
FIG. 16 shows one component, C3, in a polarizing element group in a third arrangement of the first embodiment.

FIG. 16 shows one component, C3, in a PEG in a third arrangement of the first embodiment. Pinhole, PH, for source imaging is located on reticle back RB (as in A3, A4) along with polarizing elements SP, QW. Thickness variations in SP, QW are not important in this arrangement, only reticle thickness needs to be taken into account.

Figure 17:
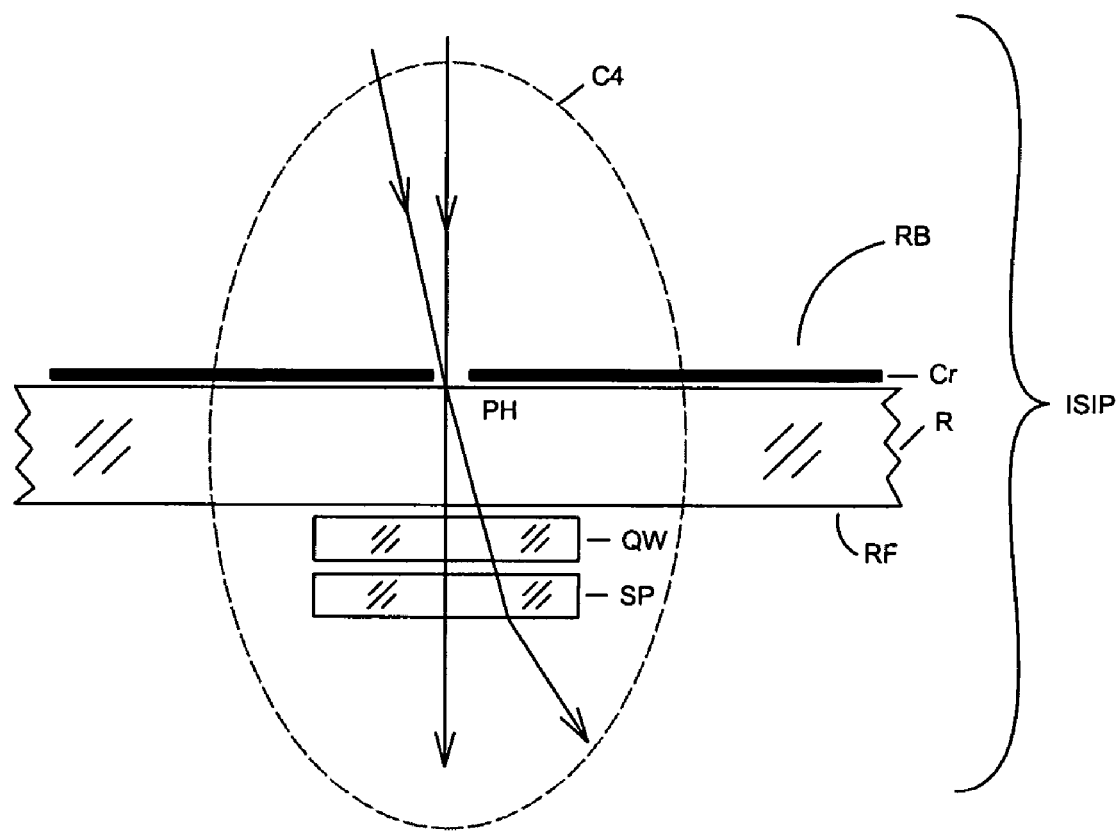
FIG. 17 shows one component, C4, in a polarizing element group in a fourth arrangement of the first embodiment.

FIG. 17 shows one component, C4, in a PEG in a fourth arrangement of the first embodiment. It consists of pinhole, PH, for source imaging on reticle backside (RB) with polarizing elements QW (quarter wave plate) and SP (sheet polarizer) on reticle face (RF). Imaging characteristics will depend on total (reticle+QW+SP) thickness and therefore we need to either tightly measure or specify this optical path length prior to assembly to account for it in the reconstruction process.

Figure 18:
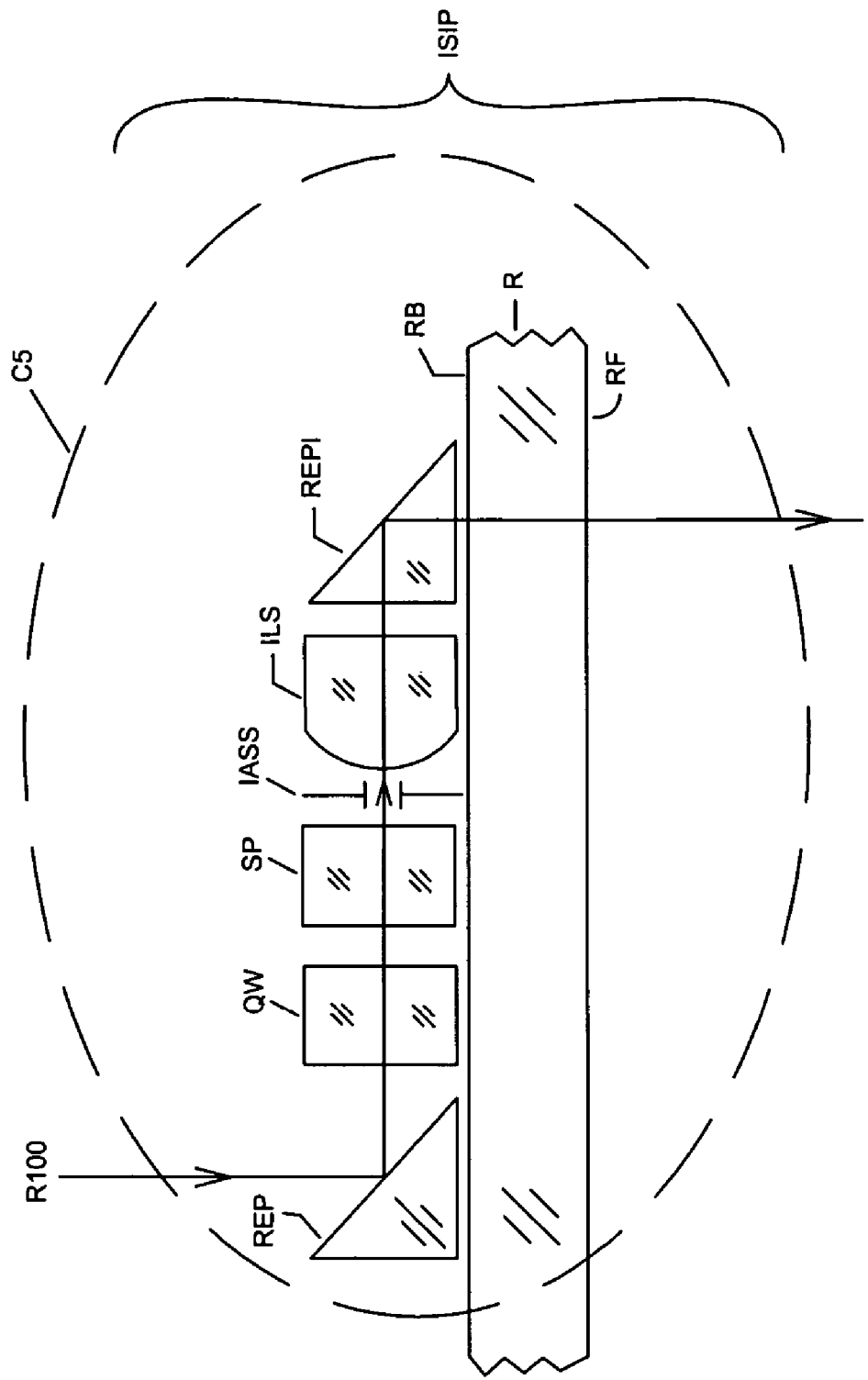
FIG. 18 shows one component, C5, in a polarizing element group in a fifth arrangement of the first embodiment.

FIG. 18 shows an iPEG (component), C5, of a multicomponent PEG in a fifth arrangement of the first embodiment. In this arrangement, an in-situ imaging objective according to see, for example, U.S. Patent Publication No. US20050231705, supra is used for the in-situ source imaging. Light (represented by ray R100) is incident on reflecting prism REP that reflects it to a direction substantially parallel to reticle backside RB. Then quarter wave plate, QW, is followed by sheet polarizer, SP, after which in-situ imaging objective aperture stop, IASS, sets the numerical aperture (NA1) for source imaging resolution. Next, source imaging lens ILS images the effective source onto reticle face, RF, after the light passes through reflective prism operating on internal reflection, REPI, (could use total internal reflection or aluminized external coating). The reason for bending light with REP is to fit entire optical package above reticle back, RB, within mechanical constraints of the projection imaging system.

Figure 19:
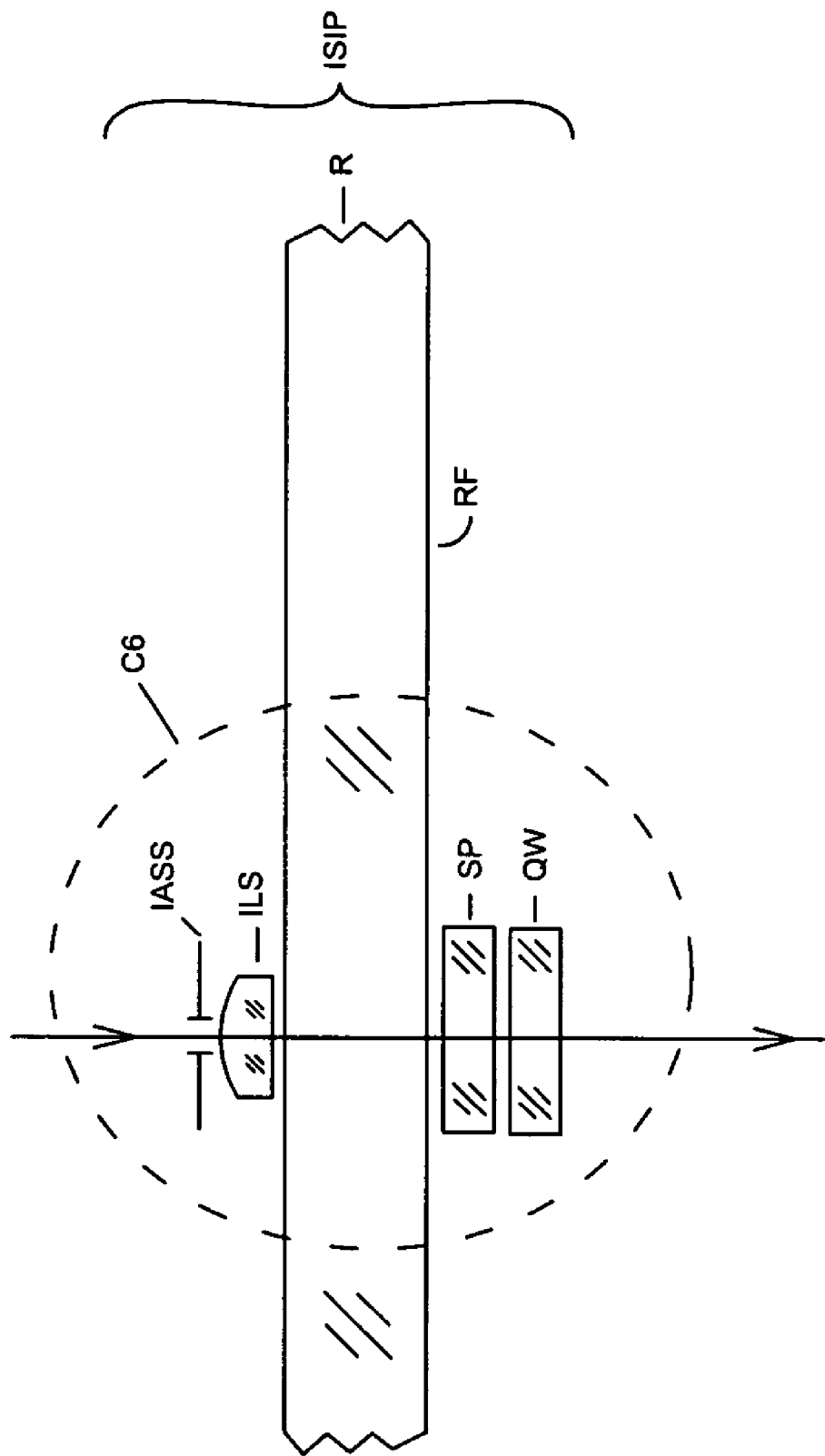
FIG. 19 shows one component, C6, in a polarizing element group in a sixth arrangement of the first embodiment.

In a sixth arrangement for the first embodiment, FIG. 19 shows one component, C6, that utilizes an in-situ imaging objective consisting of aperture stop IASS and imaging lens ILS that images the effective source, ES, just short of reticle face, RF. These are followed by the polarizing elements of sheet polarizer, SP, and quarter wave plate, QW. Thickness of SP and QW must be taken into account for determining amount short of RF that source is imaged to.

Figure 20:
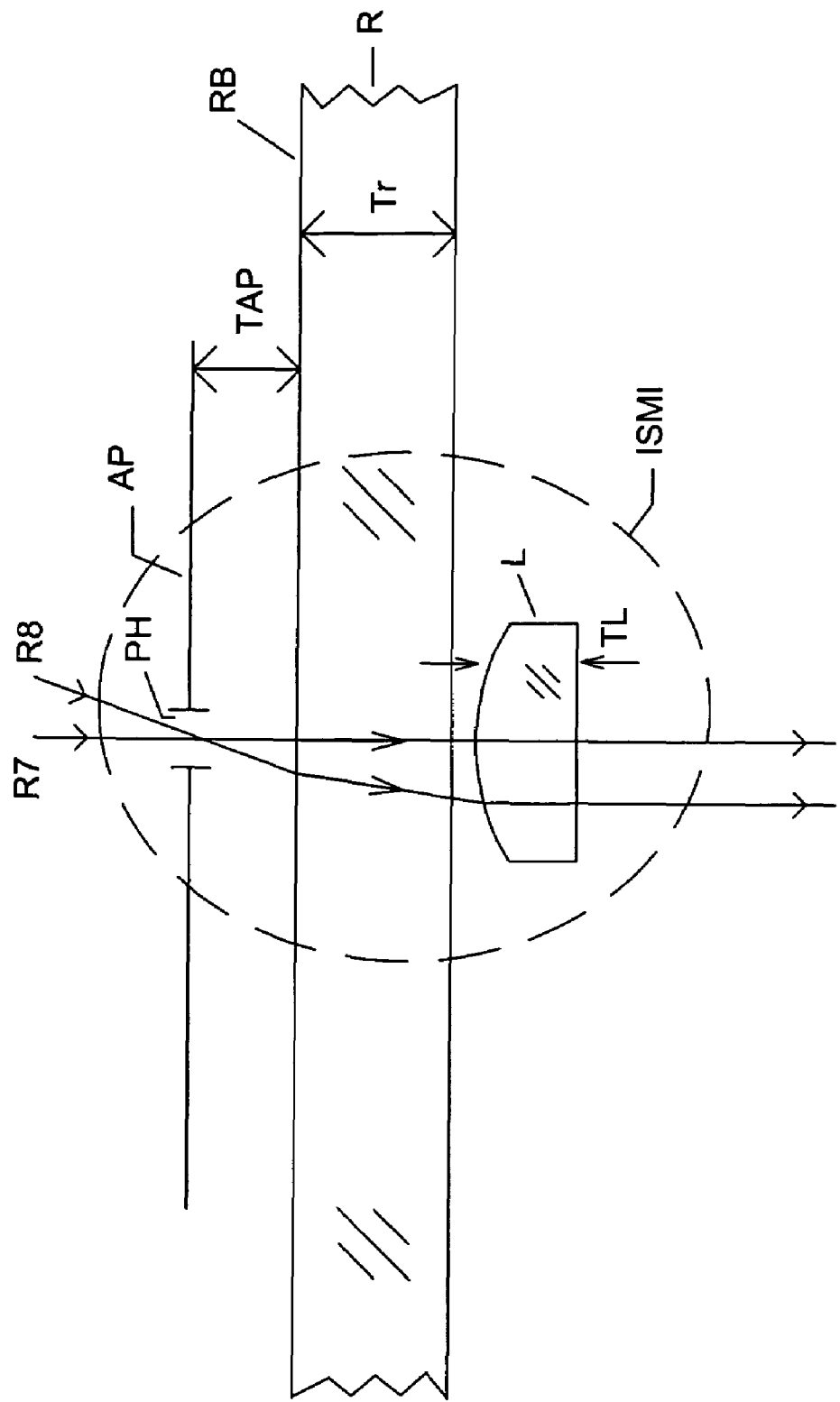
FIG. 20 shows an infinity imaged in-situ source metrology instrument (ISMI) using a lens, L.
Figure 21:
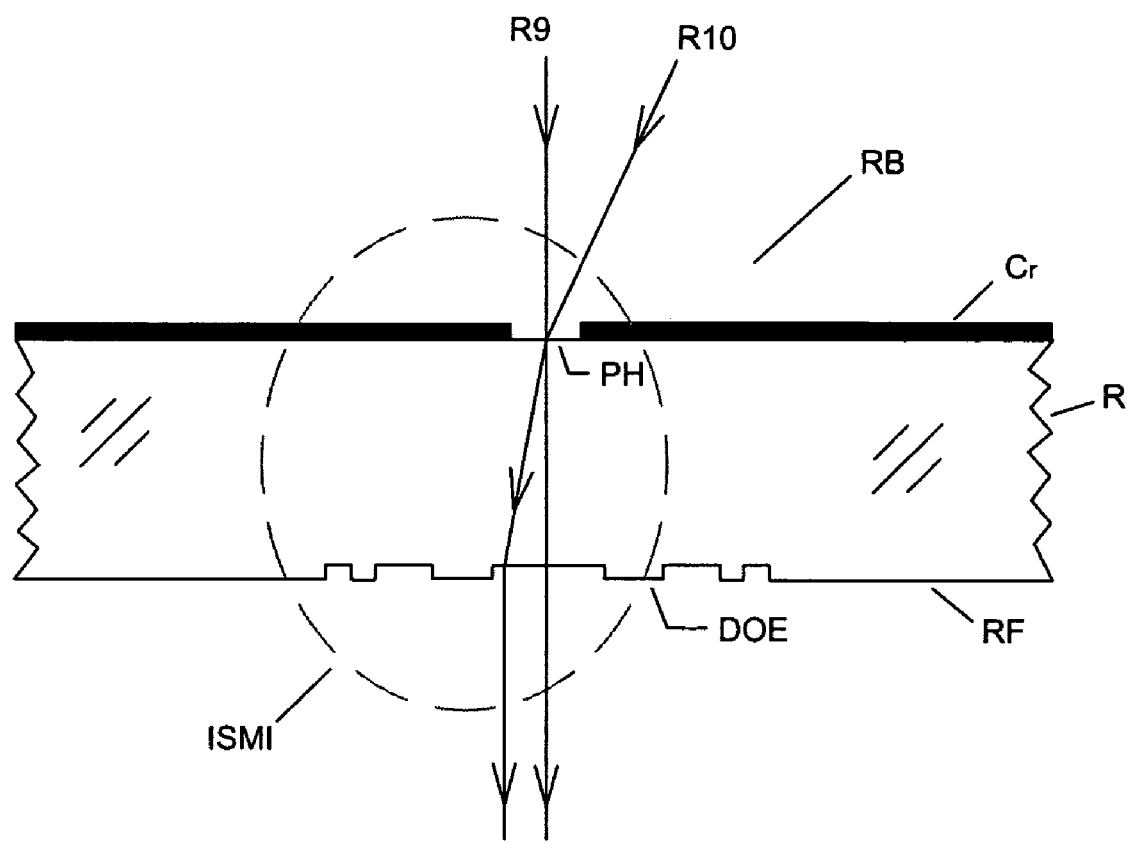
FIG. 21 shows an infinity imaged in-situ source metrology instrument, ISMI, utilizing a diffractive optical element, DOE.

Another sort of in-situ source metrology instrument (ISMI) is shown in FIG. 20. In operation light from ES (represented by rays R7 & R8) is incident on pinhole PH in aperture plate, AP, located on or above reticle backside, RB. Lens, L is set to image pinhole PH to infinity (i.e., chief rays R7 & R8 emerge as parallel rays after passing through L). In this manner, angular position within the source is encoded as transverse position on the reticle but the angular diversity of rays passing into projection imaging optic PIO (not shown) is set not by the angular size of the source but instead by the pinhole numerical aperture (NAph). We call this class of arrangement an infinity imaged ISMI (see FIG. 3). One motivation for this sort of arrangement is to minimize the influence of lens transmission variation on the final answer (vide supra) but also to widen the range of polarizing devices that can be utilized in the practice of this invention (vide infra). FIG. 21 shows another variation of the infinity imaged in-situ source metrology instrument. It uses a diffractive optical element (DOE) to collimate light coming from pinhole PH.

Figure 22:
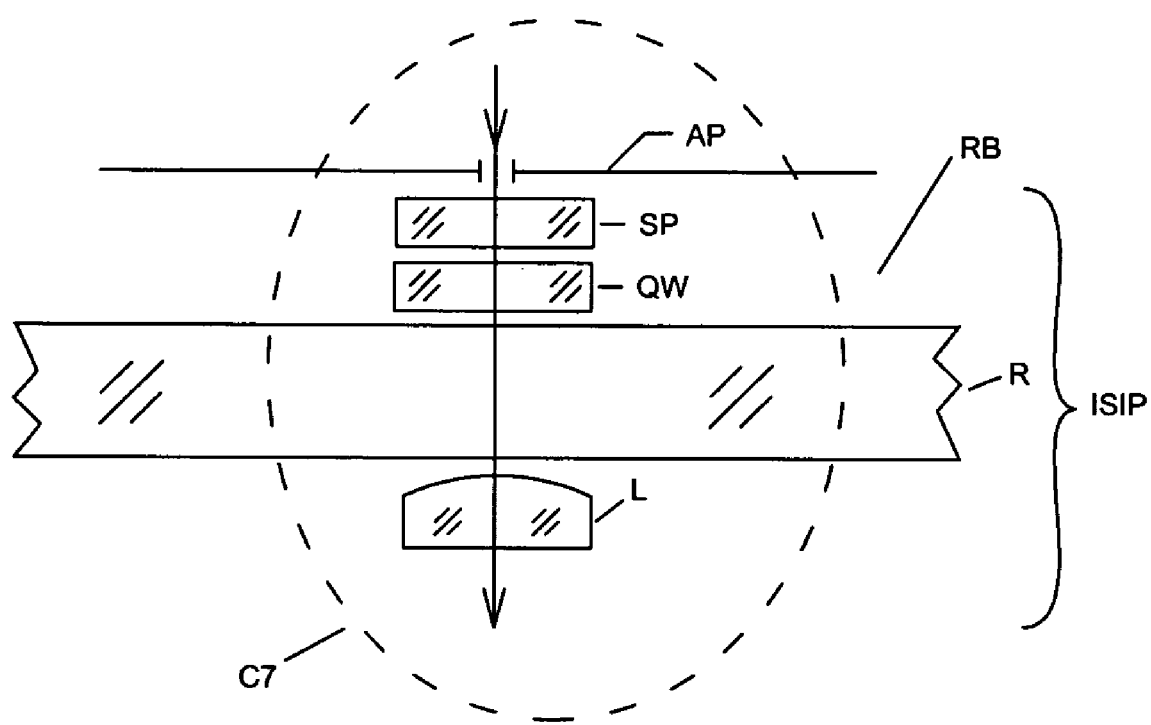
FIG. 22 shows one polarizing component, C7, in a polarizing element group in a seventh arrangement of the first embodiment.

An application of infinity imaged ISMI to a PEG is shown in FIG. 22 where component C7 (iPEG) has a sheet polarizer, SP, and quarter wave plate, QW, disposed between aperture plate, AP, and reticle back, RB.

Second Embodiment

This second embodiment differs from the first embodiment mainly in utilizing a polarizing beam splitter cube (PBS) as the polarizing element in place of sheet polarizers, SP. Wave plates used in the foregoing arrangements are again specially cut uniaxial crystalline plates. The flow diagram is similar to FIG. 4c (Blocks 1-5) and is now described.

Provide In-Situ Polarizers

Applicability of polarizers is a strong function of the range of incident angles (field of view or FOV) over which it must operate. For projection imaging tools the half angle of the cone of light from effective source, ES, impinging on reticle, R is in the range of 5-20 degrees. A typical commercial PBS might have a 2.5 degree FOV that may be useable (depending on the interface coating details) out to ~5 degrees FOV with 50:1 extinction and in reflection only (see, for example, "CVI UV Polarizing Beamsplitter Cubes", CVI Laser Optics/New Focus). More specialized narrow wavelength band designs can work at up to 15 degrees FOV (see, for example, Baumeister, "Rudiments of the design of an immersed polarizing beam divider with a narrow spectral bandwidth and enhanced angular acceptance", Applied Optics, Vol. 36, No. 16, pp. 3610-3613, June 1997). For even greater field views, beam splitters using frustrated total internal reflection (see, for example, Li, "The Design of Optical Thin Film Coatings", Optics & Photronics News, pp. 24-30, September 2003 and Li et al., "High-performance thin-film polarizing beam splitter operating at angles greater than the critical angle", Applied Optics, Vol. 39, No. 16, pp. 2754-2771, June 2000) can be fabricated at wavelengths where suitable thin dielectric films are available; greater FOV in transmission is also achievable if we do not constrain the prism interface angle to 45 degrees, but adjust it for optimal performance. Because of the wide FOV constraint general imposed by our application, the PBS need only produce high (>50:1) polarization ratios for only one beam (usually transmitted).

Provide In-Situ Source Metrology Instrument

Figure 23:
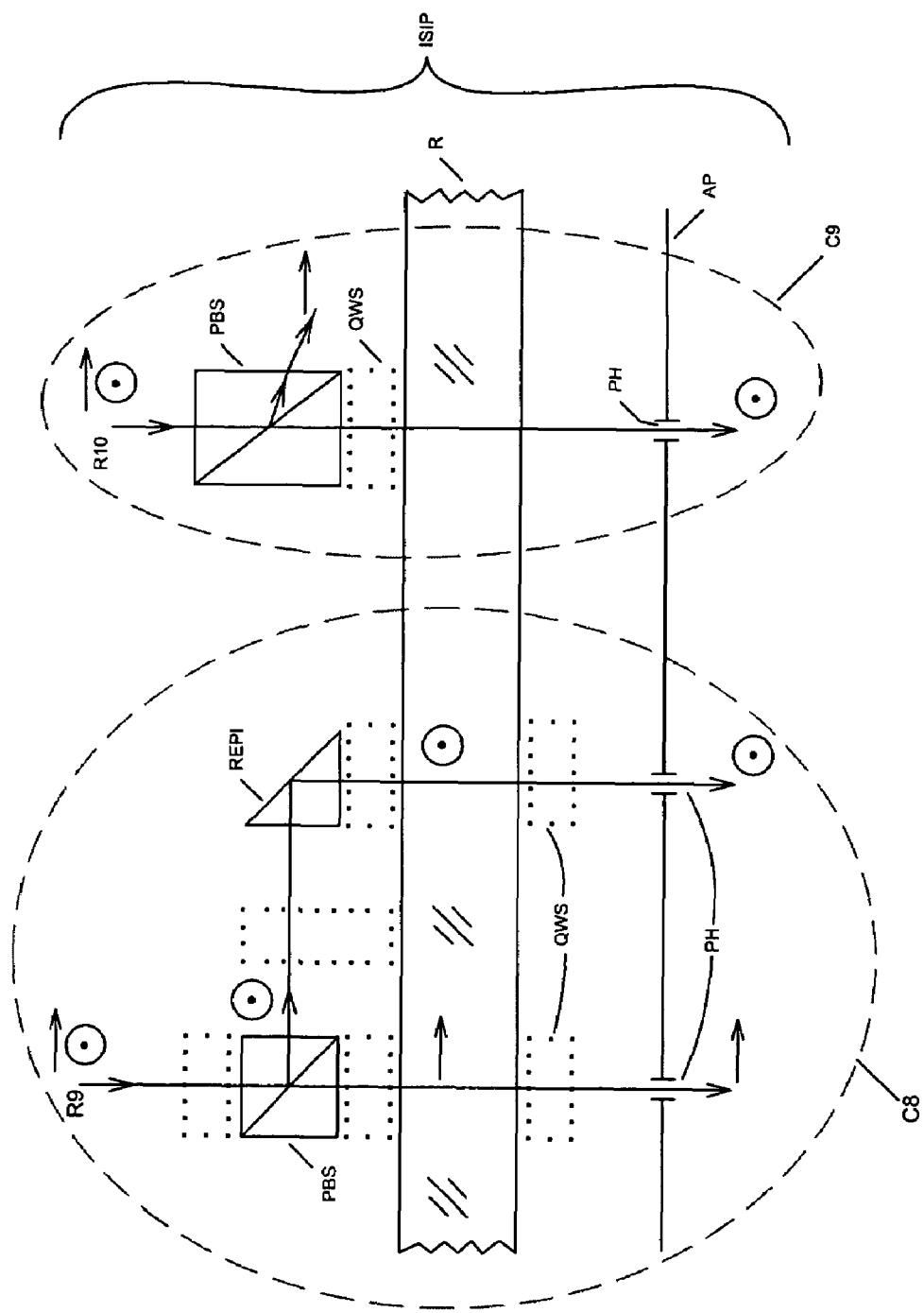
FIG. 23 shows several arrangements for polarizing components in a second embodiment.

FIG. 23 shows several arrangements for polarizing components. Dotted rectangles denote possible locations of quarter wave plates (QWS or quarter wave plate sites) in these arrangements. C8 contains two components of a PEG that utilizes a wide angle, 45 degree polarizing beam splitter, PBS. Each polarization produced by PBS is separately imaged by different pinholes PH. C9 is a single component of a PEG utilizing a wide angle, non-45 degree PBS that is optimized only for high polarization of the transmitted light.

Figure 24:
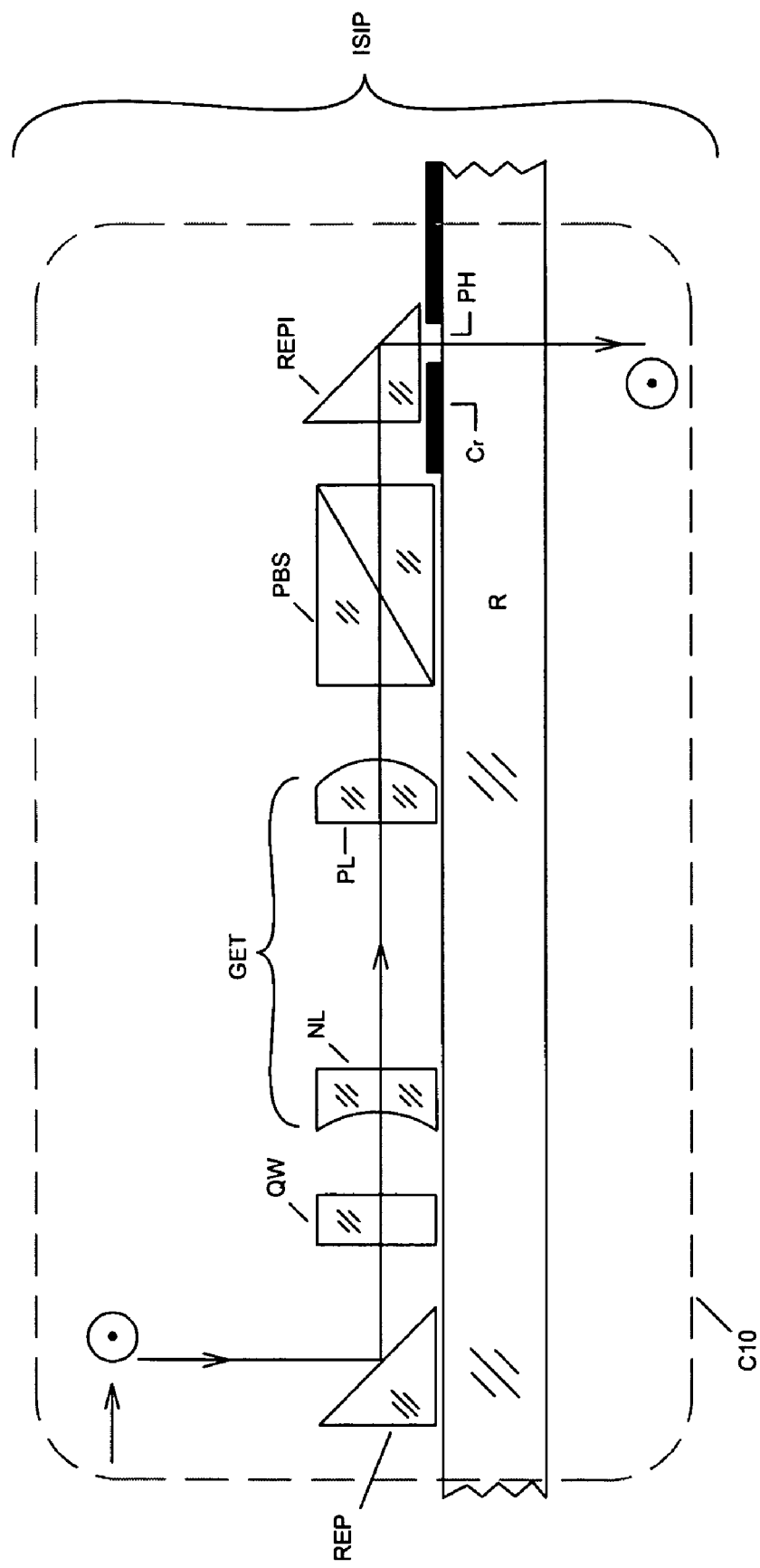
FIG. 24 shows another arrangement for the second embodiment. C10 is a component of a polarizing element group that utilizes a Gallilean expansion telescope to reduce the net source input angle range incident on polarized beam splitter PBS.

FIG. 24 shows another arrangement for the second embodiment. C10 is a component of a PEG that utilizes Gallilean expansion telescope GET (see, for example, Born et al., "Principles of Optics, 7$^{th}$ (expanded) Edition", *Cambridge University Press*, pp. 268-269, 2001) to reduce the net source input angle range (FOV) incident on polarized beam splitter PBS. FOV reduction eases performance criteria required of PBS. GET is comprised of negative lens NL and positive lens PL.

Figure 25A:
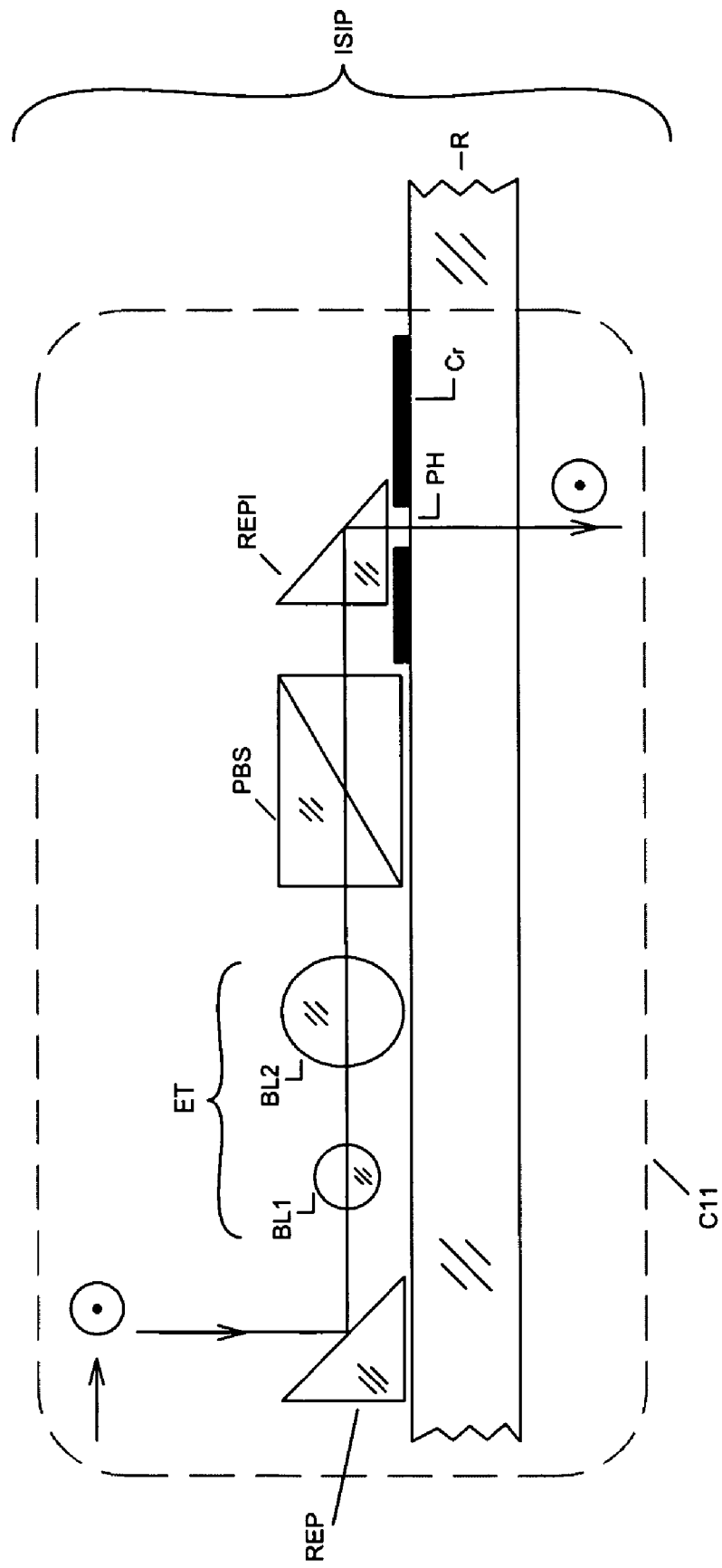
FIG. 25a shows yet another arrangement for the second embodiment. C11 is a component of a polarizing element group that utilizes ball lens expansion telescope to reduce source angular size.

FIG. 25a shows yet another arrangement for the second embodiment. C11 is a component of a PEG that utilizes ball lens expansion telescope ET to reduce the source angular size. Like GET, ET expands the incident beam in area by a factor of 2:4× and simultaneously reduces the angular range of the effective source by the same factor.

Figure 25B:
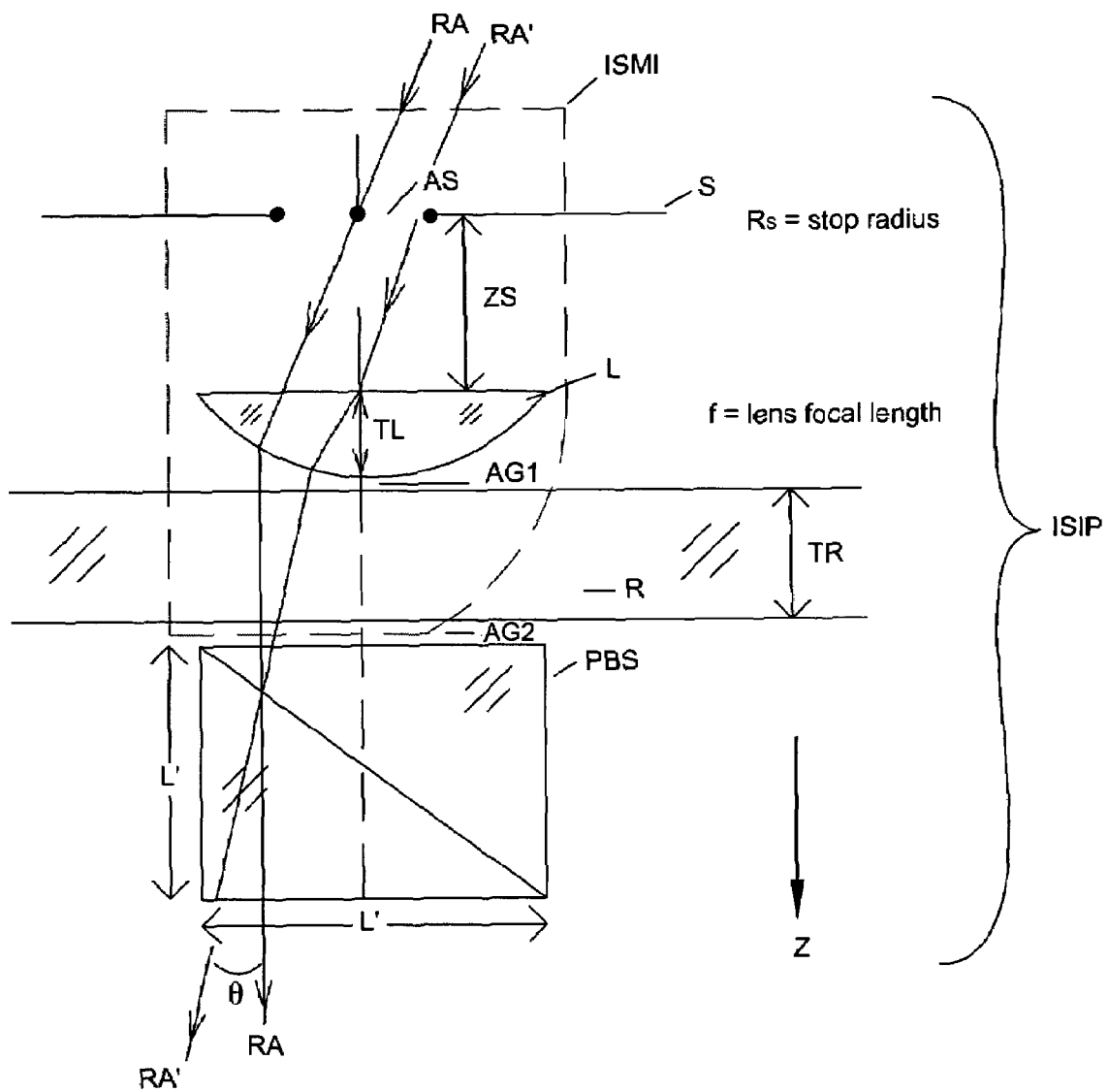
FIG. 25b shows another arrangement for the second embodiment utilizing an infinity imaged ISMI.

FIG. 25b shows still another arrangement that utilizes an infinity imaged ISMI (outlined by dashed line) combined with polarized beam splitter PBS. In accordance with the construction of infinity imaged ISMI (vide supra) lens L in ISMI images aperture stop AS to infinity. Put differently, exemplary source ray, RA, coming from effective source ES (not shown) passing through center of AS is refracted by lens L such that it emerges from L substantially parallel to the Z direction (which coincides with the optical axis of the projection imaging tool). Similarly (supra), ray RA' from ES that passes through edge of aperture stop AS emerges from bottom of PBS at an angle $\theta \approx NA_{Ph} \approx R_{stop}/f$ where $R_{stop}$ is radius of aperture stop AS and f the focal length of lens L. So far we are repeating in the present context operation of infinity imaged ISMI. After ISMI, polarized beam splitter, PBS, is placed. In transmission mode (shown) these will be substantial (>50:1) reduction in one polarization component relative to another. Exemplary parameters for an arrangement intended to operate at wavelength λ=193.3 nm out to a maximum source angle of 20.7° are given in Table 1.

TABLE 1

Exemplary constructional parameters for arrangement of FIG. 25.1. Units are millimeters.

| Symbol | Meaning | Value |
|---|---|---|
| $R_{stop}$ | aperture stop radius | 0.075 |
| ZS | stop to lens distance | 1.80 |
| TL | lens center thickness | 0.60 |
| AG1 | lens to reticle airgap | 0.05 |
| TR | reticle thickness | 3.81 |
| AG2 | reticle to polarized beam splitter airgap | 0.05 |
| L' | polarized beam splitter cube size | 2.0 |

The arrangement of Table 1 produces an angle θ between ray RA and RA' of 2°. This allows for very conventional coatings and standard constructions to be used for the PBS.

Inclusion of quarter wave plates is straightforward; they are placed after PBS of FIG. 25b.

Blocks B13, B14

This is the same as in the first embodiment.

Block B15

This is the same as in the first embodiment except when we use expansion telescope ET or GET we must take the magnification factor explicitly into account to arrive at the correct result for polarization matrix.

Third Embodiment

The third embodiment differs from the first and second embodiments mainly in using one or more polarizing reflecting prisms (PRP) as polarizing elements. Waveplates are as previously described. Some aspects of reflective, thin film polarizers are discussed in see, for example, Thomsen et al., "Polarizing and reflective coatings based on half-wave layer pairs", *Applied Optics*, Vol. 43, No. 22, pp. 4322-4327, Jan. 1, 1997. Again see the flow diagram in FIG. 4c.

Provide In-Situ Polarizers, Provide In-Situ Source Metrology Instrument

Figure 26:
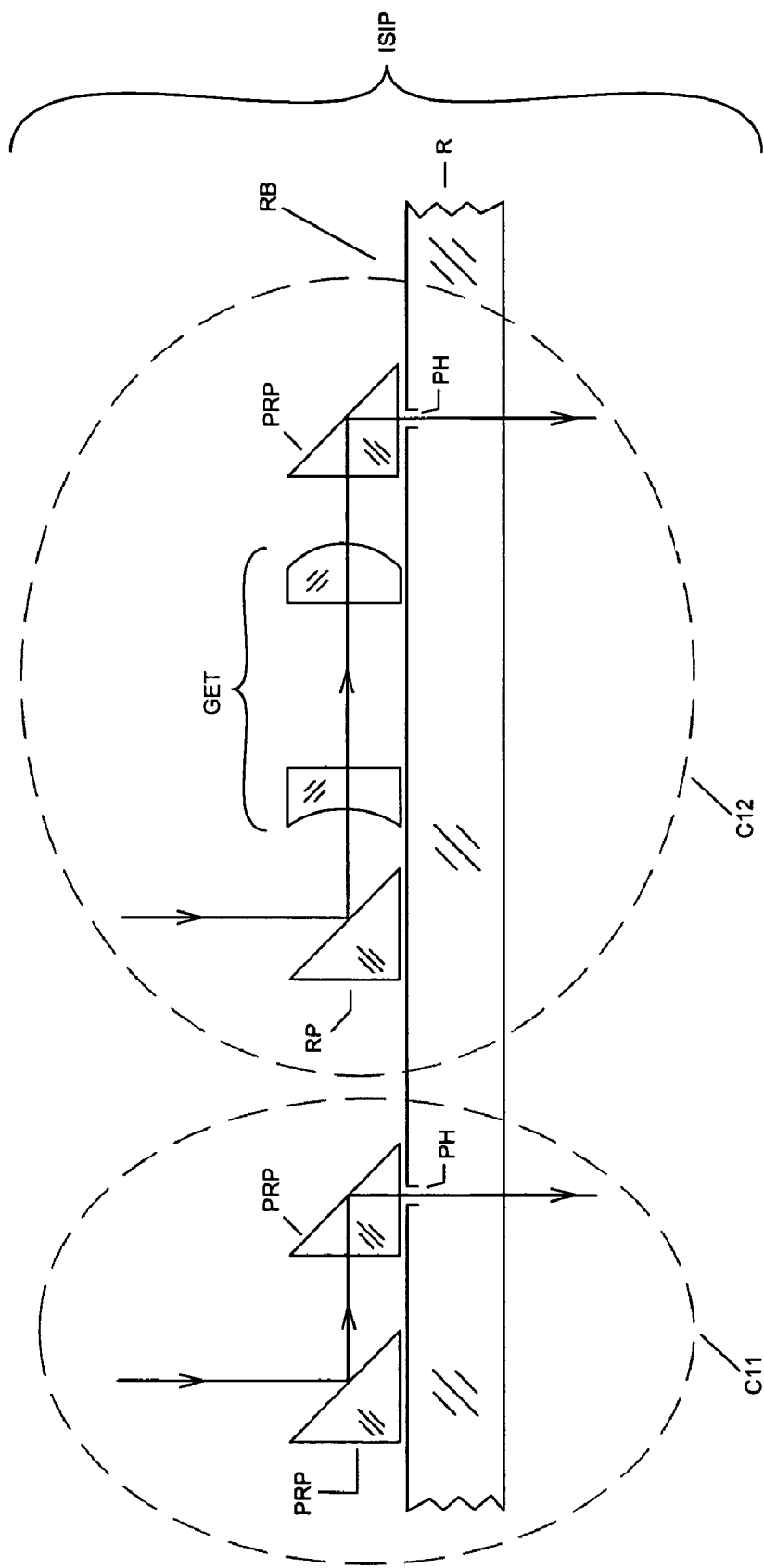
FIG. 26 shows two arrangements of a polarizing element group in a third embodiment that utilizes polarizing reflecting prisms.

FIG. 26 shows two arrangements for components in a PEG utilizing polarizing reflecting prisms. C11 uses a pair of polarizing prisms (PRP) and a pinhole in the reticle back, RB, while arrangement C12 utilizes a PRP that is preceded by Gallilean expansion telescope (GET) that reduces the FOV requirements on PRP.

Figure 27:
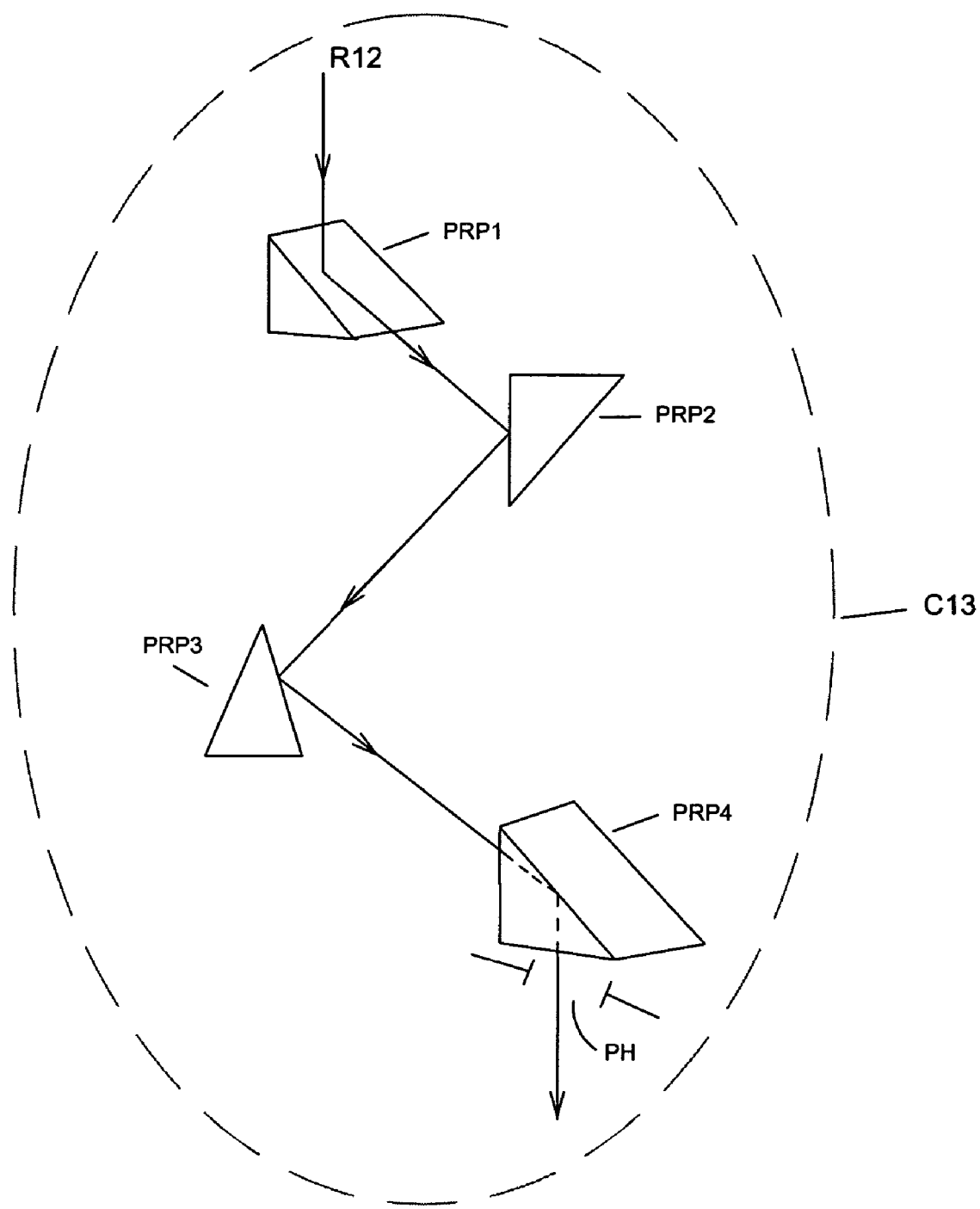
FIG. 27 shows a perspective view of a third arrangement of the third embodiment that utilizes a sequence of >2 polarized reflecting prisms.
Figure 28:
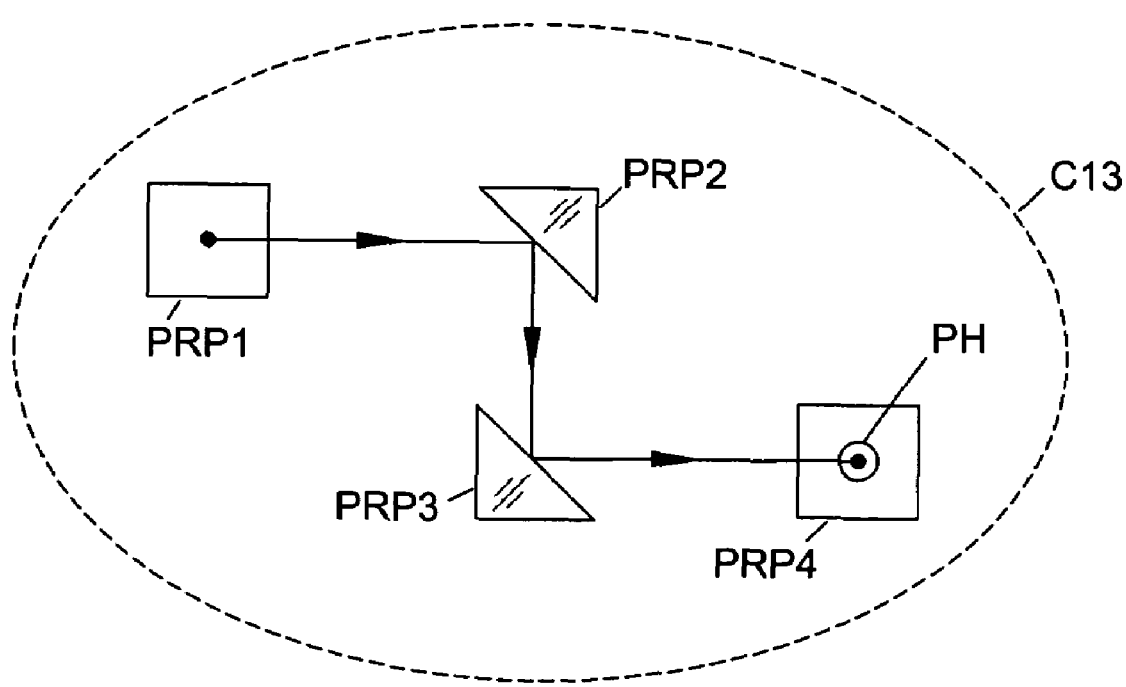
FIG. 28 shows a plan view of a third arrangement of a third embodiment looking down on the reticle top.

FIGS. 27 and 28 show a perspective and plan views of a third arrangement that utilizes a sequence of >2 polarized reflecting prisms. PRP1, PRP2, PRP3, PRP4 are mounted in the same plane on the reticle top or reticle back. In FIG. 28, light along the component optical axis (indicated by arrow) is incident on PRP1 from above the plane of the page, then stays in the plane passing from PRP1 to PRP4, thereafter moving perpendicularly away from the plane of the page and passing through pinhole PH located on the reticle back, RB.

Blocks 3:5

Blocks three through five in FIG. 4c are as discussed above.

Fourth Embodiment

The fourth embodiment differs mainly in using wire grid polarizers (see, for example, Hecht, "Hecht, Optics Polarization and Wire Grid Polarizers", Second edition, Addison Wesley Publ, ISBN: 0-201-11609-X, p. 279, May 1990) as the polarizing elements. Waveplates are as previously discussed and we can refer to FIG. 3 for the block descriptions.

Provide In-Situ Polarizers

Figure 29:
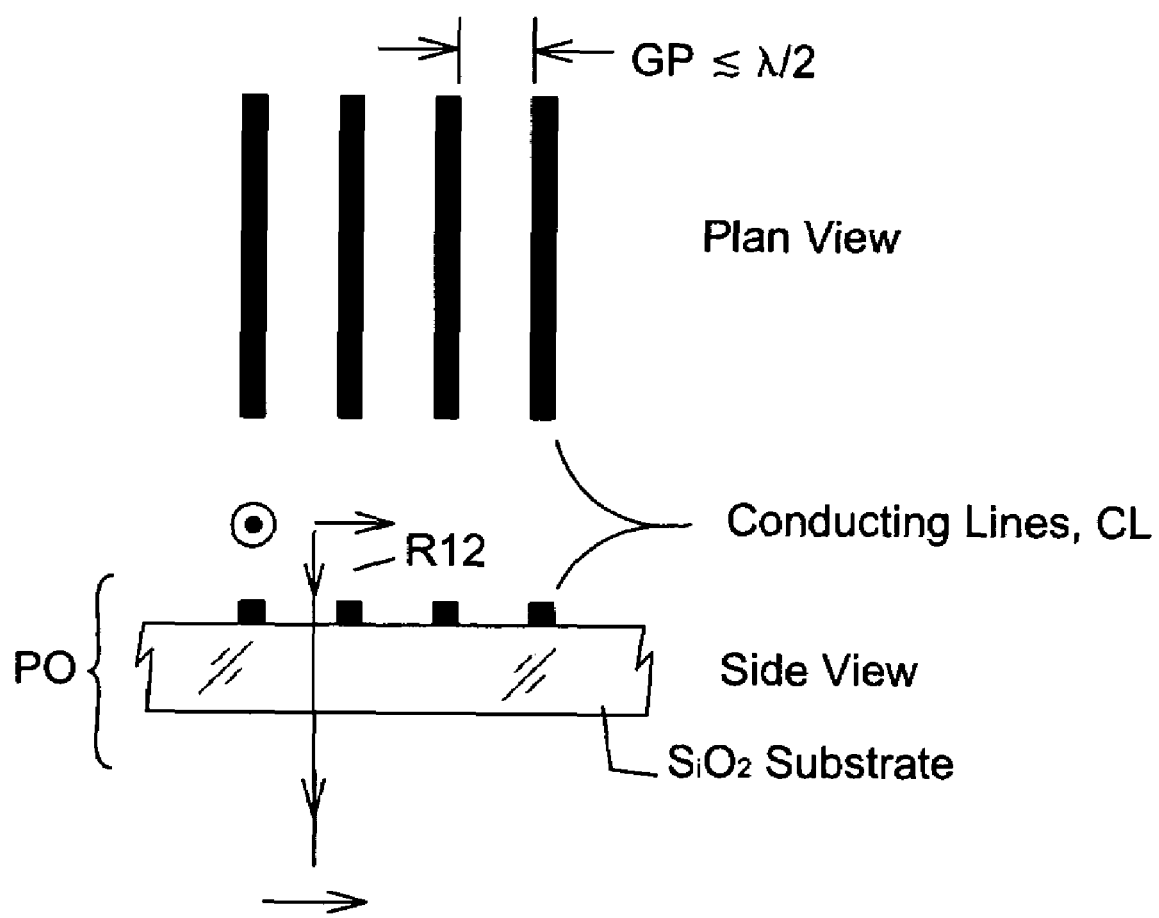
FIG. 29 shows plan and side views of polarizing element PO consisting of multiple parallel conduction lines (wire grid) on a transmitting substrate.

FIG. 29 shows a plan and side view of a reflective polarizing element PO consisting of multiple parallel conducting lines (wire grid) on a transmissing substrate. Pitch, GP, of conducting is typically ≦ wavelength/2. This insures there are no propagating orders other than the zero order and it is also the regime where there is high polarization discrimination (see, for example, Miyake et al., "LPP-based reflectometer for EUV lithography"). Light incident, R12, on PO and polarized parallel to the wires is substantially reflected while the orthogonal polarization is substantially transmitted. The elements can be used in optical arrangements in a manner substantially similar to sheet polarizers of the first embodiment or when used in reflection, as in the third embodiment.

Figure 30:
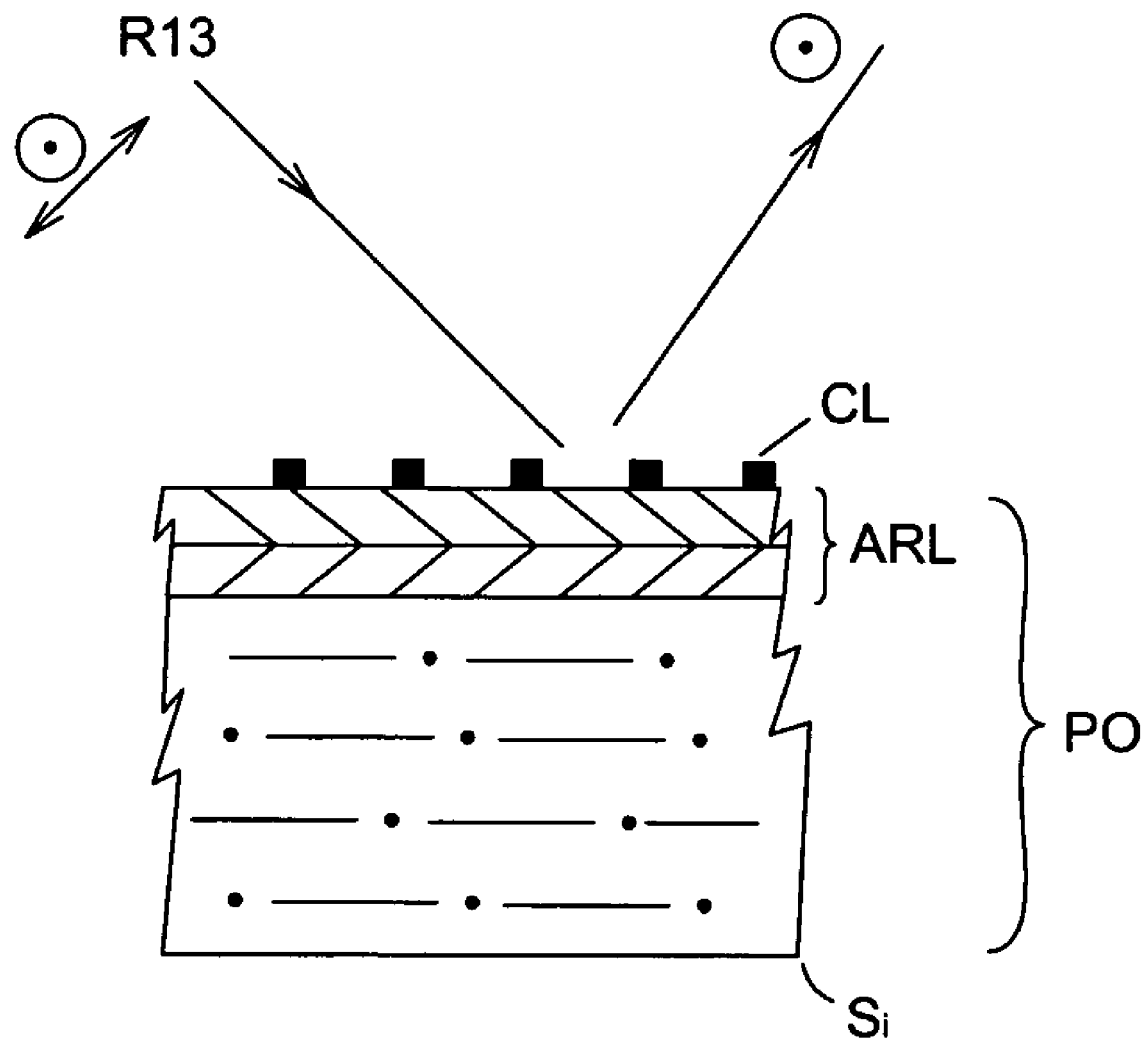
FIG. 30 shows in cross sectional view a polarizing optic that works in reflection only and is fabricated on a silicon wafer.

FIG. 30 shows a plan view of polarizing optic, PO, that works in reflection only. Silicon (Si) substrate with antireflection or reflection minimizing layer (for out of plane polarization) and conducting lines (CL) acts as a poor reflector to light polarized in the plane of incidence and as a good reflector to light polarized perpendicular to the plane of incidence.

Blocks 3:5

Blocks three through five in FIG. 4c are as described above.

Fifth Embodiment

Figure 31:
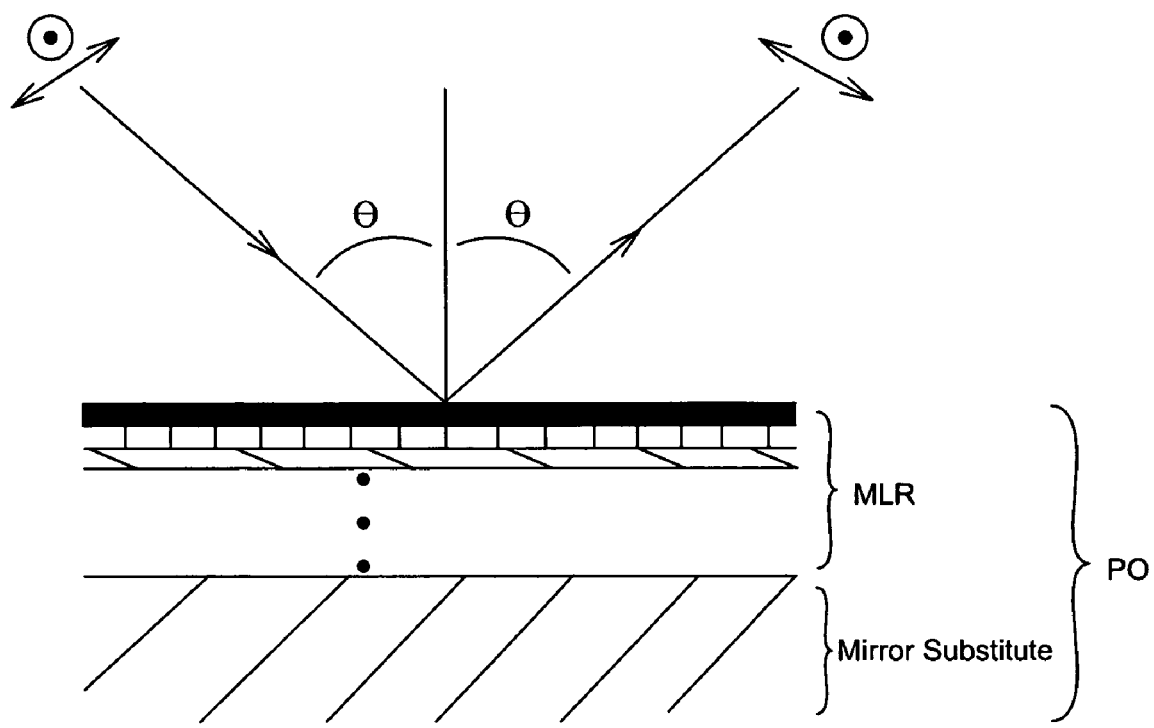
FIG. 31 shows a multilayer reflector operating at approximately Brewster's angle acting as a partial polarizer.

The fifth embodiment is aimed towards EUV (wavelength=5:100 nm and particularly 13 nm) projection imaging tools. The optical arrangement contains reflective surfaces only (see, for example, Harned et al., "progress report: Engineers take the EUV lithography challenge", available at the URL of oemazazine.com/fromTheMagazine/feb03euv.html, 2003) but for purposes of in-situ source metrology (see, for example, U.S. Pat. Nos. 6,356,345, supra and 6,741,338) can contain metal plates with pinholes. As discussed in see, for example, Schwartz, "Polarizers for extreme Ultraviolet Light", *Physics* 7810, 2001, the most practical form of polarization is currently multiplayer reflectors (MLR) (FIG. 31) operating at an angle theta~Brewester's angle~45 degrees that acts as a partial polarizer. Polarization in the plane of incidence is greatly diminished on reflection. The field of view of such a polarizer is approximately the same as required for an NA=0.2/M=4 projection imaging objective, namely≦3 degrees.

Figure 32:
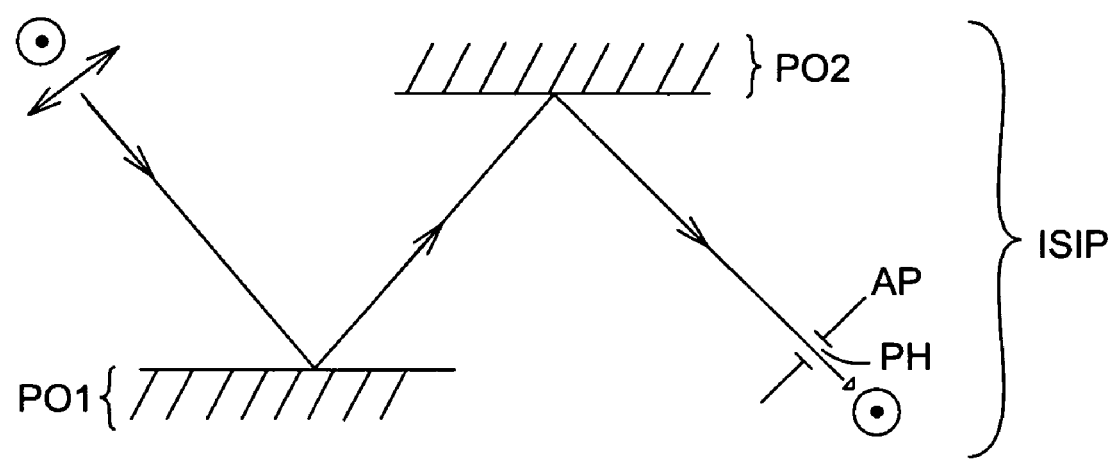
FIG. 32 shows an EUV in-situ source imaging polarizer.

An arrangement suitable for the practice of this invention is shown in FIG. 32 where polarized light hits polarizing optic PO1, then is reflected to the nominal reticle position at which is placed polarizing optic PO2 and then incident on separately inserted aperture plate, AP, containing pinhole PH. Lack of practical waveplates in the EUV means we can still recover some information (P11, P22) in the source polarization matrix.

Sixth Embodiment

There are various birefringent polarizers available in the UV:DUV wavelength region. Examples include Rochon Prisms (see, for example, "Rochon Prism", available at the URL of www.klccgo.com/mfrochon.htm), Glan Taylor Prisms (see, for example, "Glan Taylor Prisms", available at the URL of http://www.optosigma.com/miva/merchant.mv?Screen=PROD&Store_Code=OS&Product_Code=pg175&Category_Code=Polarizers), Glan Laser Prisms (see, for example, "Glan Laser Prism", available at the URL of www.u-oplaz.com/table/polarizingoptics02.htm), Wollaston Prisms (see, for example, Wollaston Prism", available at the URL of www.wollastonprism.com/), Glan Thompson Prisms (see, for example, "Glan Thompson Prisms", available at the URL of http://www.optosigma.com/miva/merchant.mv?Screen=PROD&Store_Code=OS&Product_Code=pg176&Category_Code=Polarizers), Brewster Angle Prisms (see, for example, "Brewster Angle Prism", available at the URL of www.klccgo.com/glbrewster.htm), Nicol Prism (see, for example, "Polarization", supra), Glan-Foucault (see, for example, "Glan-Foucault Prism", http://hyperphysics.phy-astr.gsu.edu/hbase/phyopt/polpri2.html), and beam splitting Glan Thompson Prisms (see for example, "Glan Thompson Polarizing Beamsplitter Cubes", available at the URL of http://www.redoptronics.com/glan-thompson-polarizing-beamsplitter-cubes.html). The light source wavelength will dictate prism material with amorphous $B_aB_2O_4$ (α-BBO) useable down to λ=190 nm and calcite useable down to λ=210 nm, while synthetically grown crystal quartz is useable down to λ=200 nm, $MgF_2$ to 157 nm. The limiting factor is mainly field of view of the incident light that is usefully polarized by the prism.

Figure 33:
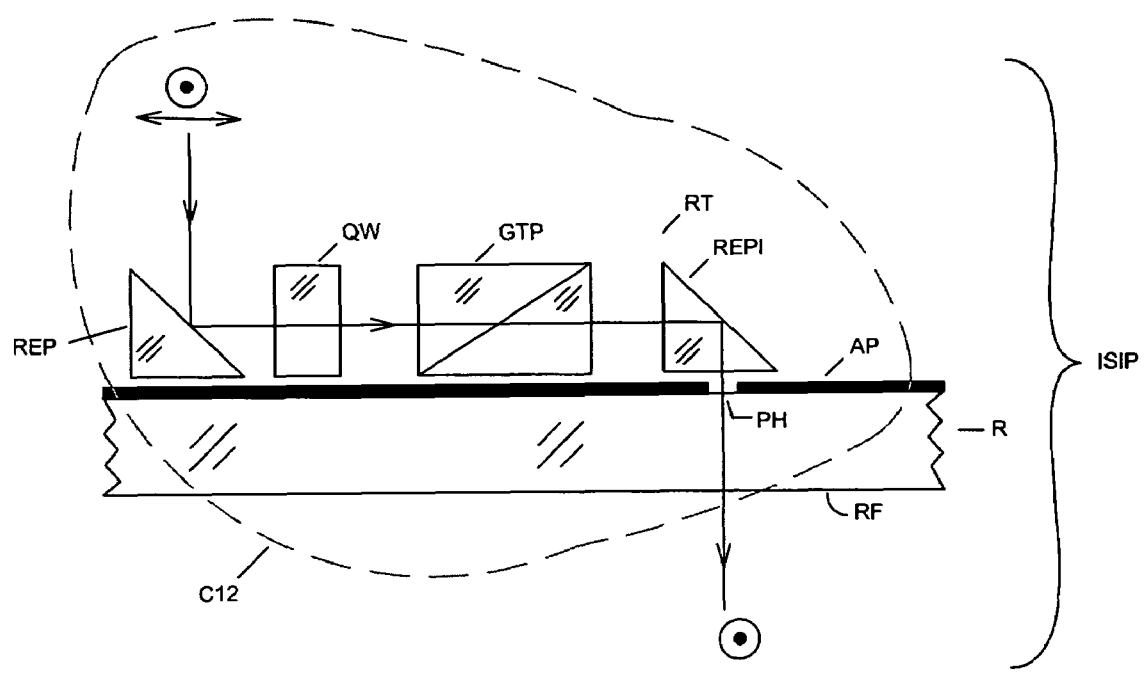
FIG. 33 shows an arrangement for the sixth embodiment where C12 is a polarizing element group component with Glan-Thompson prism polarizer (GTP).
Figure 34:
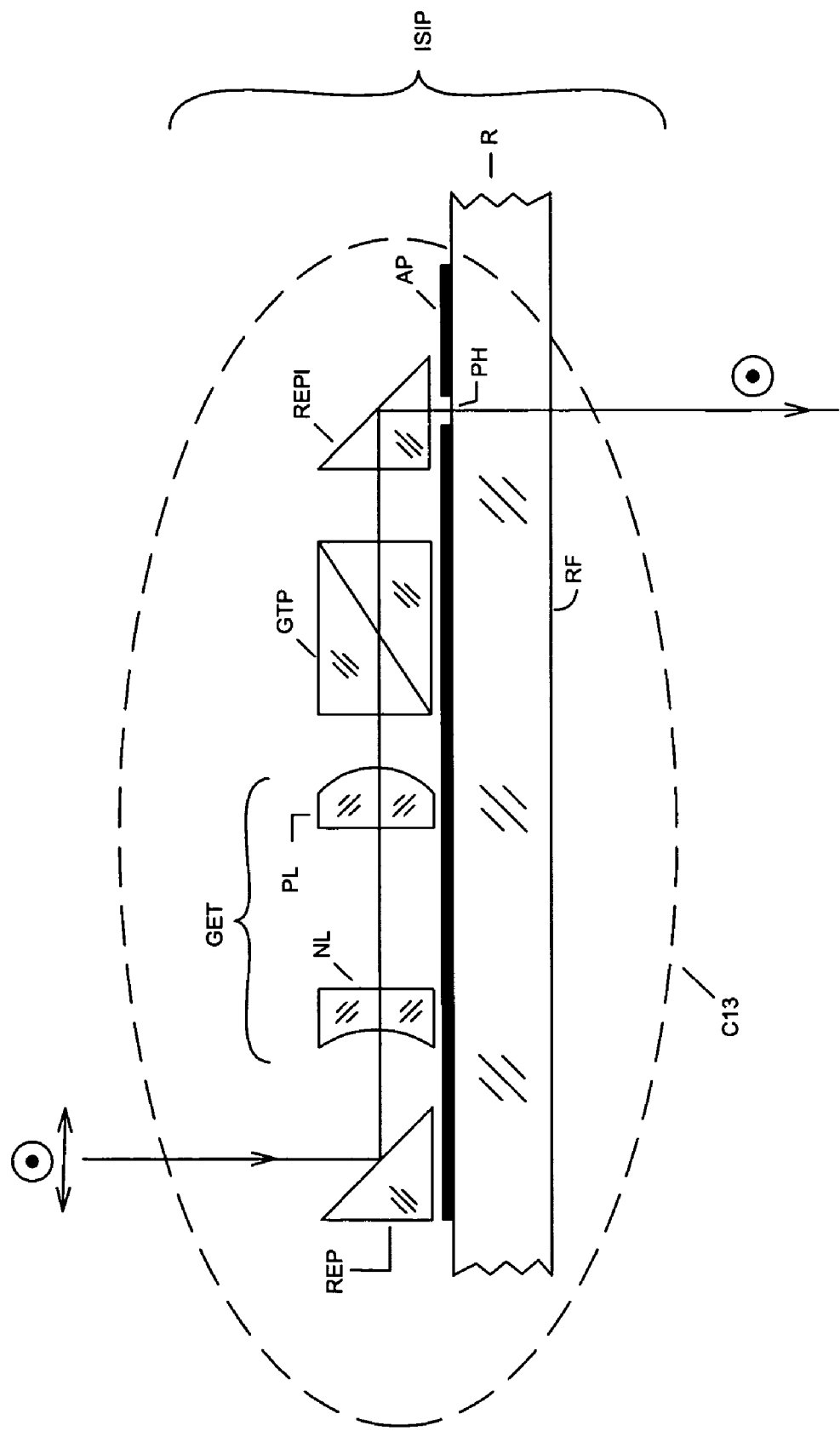
FIG. 34 shows a second arrangement for the sixth embodiment utilizing Gallilean expansion telescope (GET) to reduce effective source angular size incident on Glan-Thompson polarizing prism GTP.

FIG. 33 shows an arrangement with component C12 of a PEG that uses a Glan-Thompson prism (GTP) as the polarizing element. This arrangement is useful with smaller FOV (<10 deg) sources. It is applicable to wider angle FOVs if we utilize special thin film coatings (FTIR for example) at the prism interface. FIG. 34 shows a second arrangement for the sixth embodiment. C1 is an iPEG using Gallilean expansion telescope, GET, to reduce the net source cone angle so that a more conventional Glan-Thompson Prism (GTP) can be utilized.

Seventh Embodiment

In-situ polarizer (for example, a 0°, 90°, 45°, 45°+quarter wave plate) rotated into position in scanner body (FIG. 1) between the sub-blocks illustrated within effective source ES but most likely between input illumination optics IIO and output illuminator optics OIO. It is also possible that polarization of light source, LS, is effective in producing a known polarizing state in simpler projection imaging tools that do not contain inherent depolarizing optics.

Methods and apparatus for resolving both the angular (nx, ny) and spatial (x,y) dependence of the effective source coherence matrix (state of polarization of the source) for lithographic steppers and scanners are described. The use of a modified SMI configured with a suitable array of polarizing elements.

The foregoing description details certain embodiments of the invention. It will be appreciated, however, that no matter how detailed the foregoing appears, the invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All changes, which come with the meaning and range of equivalency of the claims, are to be embraced within their scope.

We claim:

1. A method of determining a polarization state of a source in a projection imaging system, the method comprising:
   exposing at least one in-situ polarizing element group onto a recording media with a source of unknown polarization, the in-situ polarizing element group being attached to a reticle and the in-situ polarizing element group comprising at least one polarizing element and at least one infinity imaged in-situ source metrology instrument;
   measuring an intensity at subcomponents within the exposed polarizing element group, wherein light from the source passes through projection imaging optics with unknown transmission profile before the measuring; and
   reconstructing a two dimensional angular (nx,ny) dependent polarization matrix of the source based upon the intensity measurements.

2. A method as defined in claim 1, wherein the at least one in-situ polarization element group is included in an in-situ source imaging polarizer.

3. A method of claim 2, wherein the in-situ source imaging polarizer further comprises the reticle.

4. A method as defined in claim 2, wherein the in-situ source imaging polarizer further comprises the in-situ source metrology instrument.

5. A method as defined in claim 1, wherein the recording media is located on a substrate.

6. A method as defined in claim 1, wherein the recording media comprises an electronic sensor.

7. An apparatus for determining a previously unknown state of polarization of a projection imaging tool, the apparatus comprising:
   an in-situ polarizing element group, the in-situ polarizing element group being attached to a reticle, the reticle comprising a first surface and a second surface, the second surface being disposed above the first surface, and the first surface comprising a chrome coating with at least one opening in the chrome coating; and the in-situ polarizing element group comprising at least one infinity imaged in-situ source metrology instrument and at least one polarizing element.

8. An apparatus as defined in claim 7, wherein the apparatus further comprises:
at least one lens adjacent to the second surface of the reticle;
an aperture plate mounted above the second surface of the reticle, wherein at least one opening in the aperture plate corresponds to at least one lens.

9. An apparatus as defined in claim 7, wherein the apparatus further comprises:
at least one lens adjacent to the first surface of the reticle;
an aperture plate mounted above the second surface of the reticle, wherein at least one opening in the aperture plate corresponds to at least one lens and wherein an image of the aperture plate opening is focused at infinity.

10. An apparatus as defined in claim 7, wherein the polarizing element group comprises at least two polarizing elements arranged linearly across the reticle at multiple field points.

11. An apparatus as defined in claim 7, wherein the polarizing element group is reproduced and arranged in 2-dimensional arrays across a first surface of the in-situ source metrology instrument in such a way as to cover an entire lithographic field of interest.

12. An apparatus as defined in claim 7, wherein a state of polarization of light leaving individual polarizing elements is increased or decreased by a fixed amount.

13. An apparatus as defined in claim 7, wherein at least one element of the polarizing element group comprises first and second 45-degree polarizing beam splitter elements mounted to the second surface of the reticle, wherein the first polarizing beam splitter element divides the source into two orthogonal polarization components, such that one polarization component is passed perpendicular to a Z-direction to the second beam splitter, wherein each polarizing element is aligned to a corresponding opening in an aperture plate, and wherein polarized light passes through the aperture plate opening.

14. An apparatus as defined in claim 7, wherein at least one element of the polarizing element group comprises a non-45-degree polarizing beam splitting element mounted to the second surface of the reticle, wherein the polarizing beam splitter divides the source into two orthogonal polarization components, one of which is passed through a corresponding hole in an aperture plate.

15. An apparatus as defined in claim 14, further comprising at least one quarter wave plate included with the polarizing element group that comprises two polarizing beam splitters, wherein the quarter wave plate is mounted to the reticle adjacent to and on top of the first polarizing beam splitter, under the first beam splitter on the first surface of the reticle, adjacent to and perpendicular to a Z-direction to the first beam splitter, under the second beam splitter, or under the second beam splitter on the first surface of the reticle.

16. An apparatus as defined in claim 14, further comprising at least one quarter wave plate included with the polarizing element group that comprises two polarizing beam splitters, wherein the quarter wave plate is mounted under the beam splitter on the first or second surface of the reticle.

17. An apparatus as defined in claim 7, wherein the polarizing element group comprises a polarizer placed between an input and an output illuminator.

18. An apparatus as defined in claim 7, wherein the polarizing element group comprises a light source with a known state of polarization.

* * * * *